(12) United States Patent
Froim et al.

(10) Patent No.: US 7,943,600 B2
(45) Date of Patent: May 17, 2011

(54) ANTIMICROBIAL COMBINATION THERAPY

(75) Inventors: Doriana Froim, Cambridge, MA (US); John M. Essigmann, Cambridge, MA (US); Martin G. Marinus, West Boylston, MA (US)

(73) Assignees: Massachusetts Institute of Technology, Cambridge, MA (US); University of Massachusetts, Boston, MA (US)

( * ) Notice: Subject to any disclaimer, the term of this patent is extended or adjusted under 35 U.S.C. 154(b) by 276 days.

(21) Appl. No.: 11/314,186

(22) Filed: Dec. 20, 2005

(65) Prior Publication Data

US 2006/0193924 A1    Aug. 31, 2006

Related U.S. Application Data

(60) Provisional application No. 60/637,790, filed on Dec. 20, 2004.

(51) Int. Cl.
| | |
|---|---|
| *A01N 37/18* | (2006.01) |
| *A01N 55/02* | (2006.01) |
| *A01N 33/00* | (2006.01) |
| *A01N 33/18* | (2006.01) |
| *A01N 33/24* | (2006.01) |
| *A61K 31/65* | (2006.01) |
| *A61K 31/28* | (2006.01) |
| *A61K 31/13* | (2006.01) |
| *A61K 31/16* | (2006.01) |
| *A61K 31/04* | (2006.01) |
| *A61K 33/24* | (2006.01) |
| *C07C 43/00* | (2006.01) |
| *C07C 49/00* | (2006.01) |
| *C07C 237/26* | (2006.01) |

(52) U.S. Cl. ........ 514/152; 514/154; 514/492; 514/579; 514/740; 552/203; 424/649

(58) Field of Classification Search .................. 514/152, 514/154, 492, 579, 740; 552/203; 424/649
See application file for complete search history.

(56) References Cited

U.S. PATENT DOCUMENTS

| 4,386,070 A | * | 5/1983 | De Vincentiis | 424/114 |
| 4,419,351 A | * | 12/1983 | Rosenberg et al. | 514/184 |
| 5,064,821 A | * | 11/1991 | Levy | 514/154 |

FOREIGN PATENT DOCUMENTS

| EP | 1 364 652 A1 | 11/2003 |
| WO | WO 02/24201 A1 | 3/2002 |

OTHER PUBLICATIONS

B. Rosenburg, L. Van Camp, T. Krigas, Inhibition of cell division in *Escherichia coli* by electrolysis products from a platinum electrode, Nature, vol. 205(1965), pp. 698-699.*
Rybak et al. 1996, Combination Antimicrobial Therapy for bacterial infections. Drugs. vol. 52(3), pp. 390-405.*
Jacobs et al., Synergism between gentamicin and mitomycin C in staphylococcal infections in mice. Chemotherapy. 1985;31(5):389-94.
Rudy et al., [Effects of disodium salt of ethylenediaminetetraacetic acid (Na2EDTA) and tetracyclines on drug resistant bacteria. Studies in vitro] Med Dosw Mikrobiol. 1991;43(3-4):127-34. Polish. Abstract Only.

* cited by examiner

*Primary Examiner* — Sreeni Padmanabhan
*Assistant Examiner* — Kara R McMillian
(74) *Attorney, Agent, or Firm* — Wolf, Greenfield & Sacks, P.C.

(57) ABSTRACT

This invention provides methods and pharmaceutical compositions for treating a subject having a condition associated with an antibiotic resistant bacterial infection. The invention includes administering to a subject a therapeutically effective combination of an antibiotic and a toxic compound (e.g., a nucleic acid damaging agent, an alkylating agent, or a heavy metal containing compound).

11 Claims, 12 Drawing Sheets

Figure 1
1a
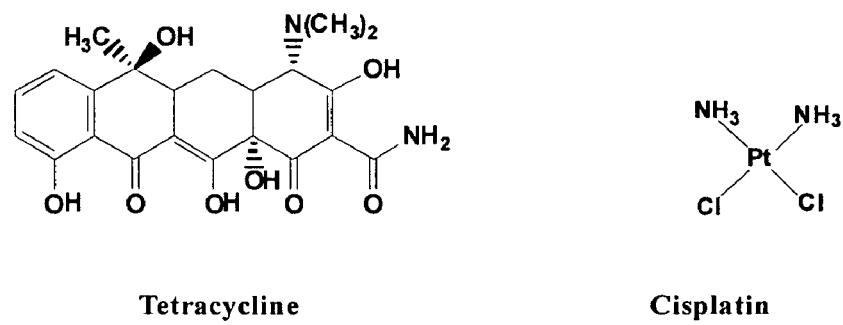
Tetracycline          Cisplatin
1b
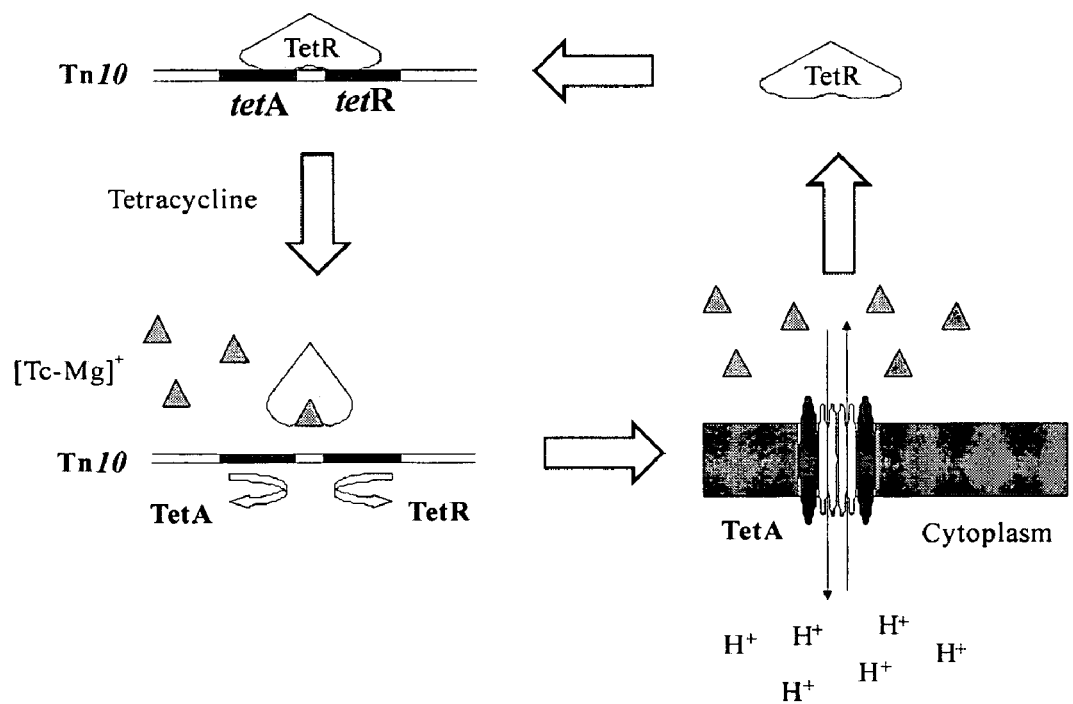

Figure 2
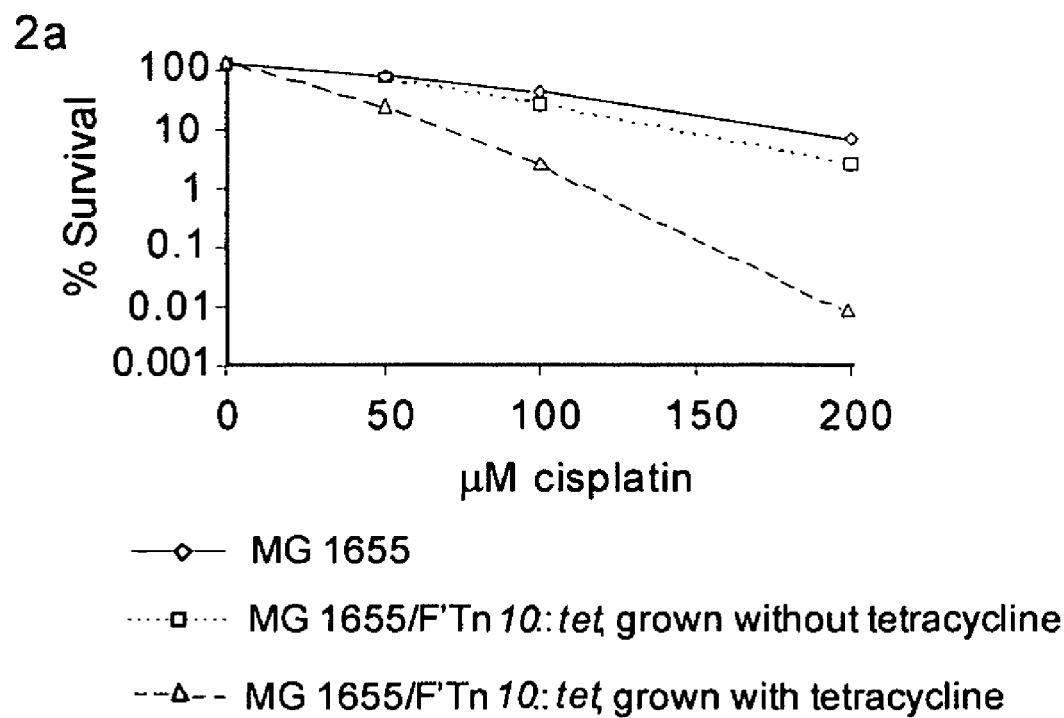
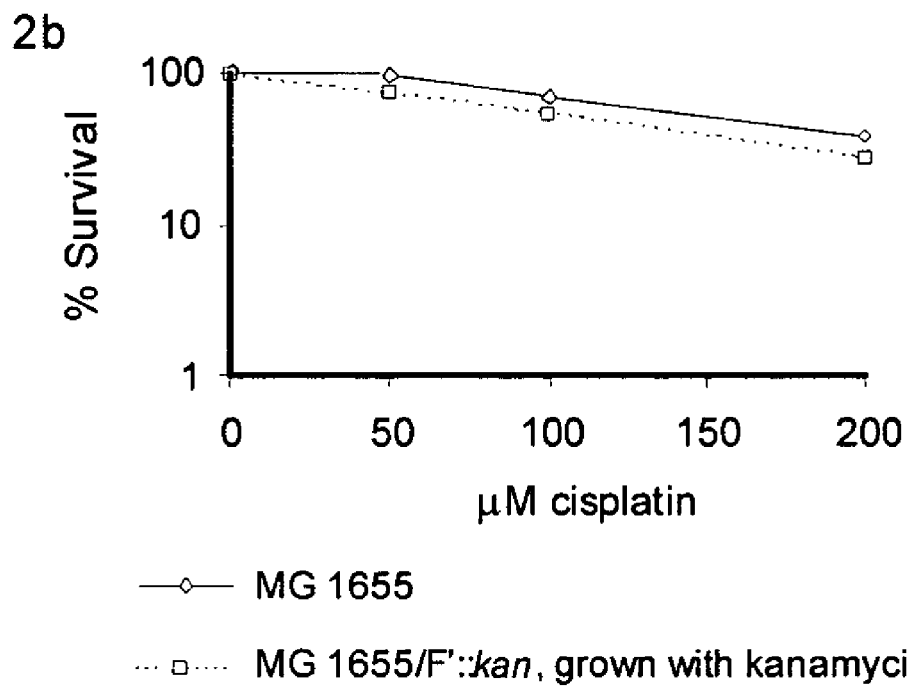

Figure 4
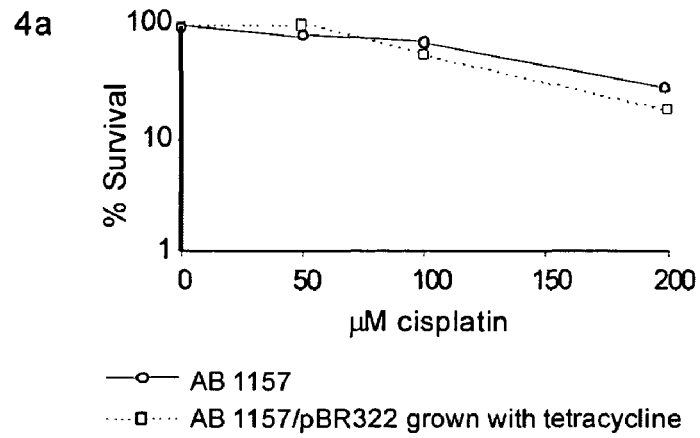
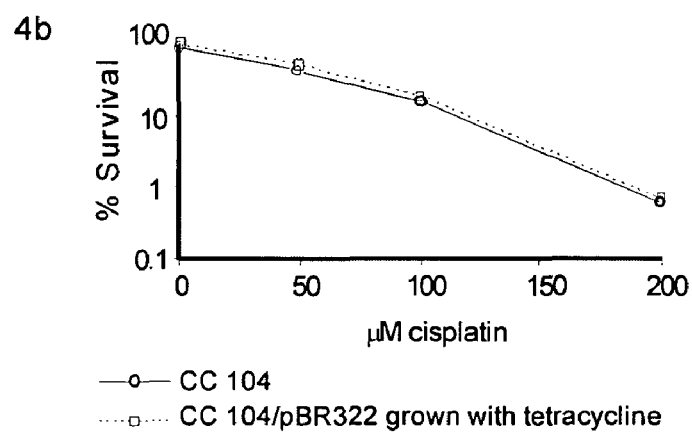
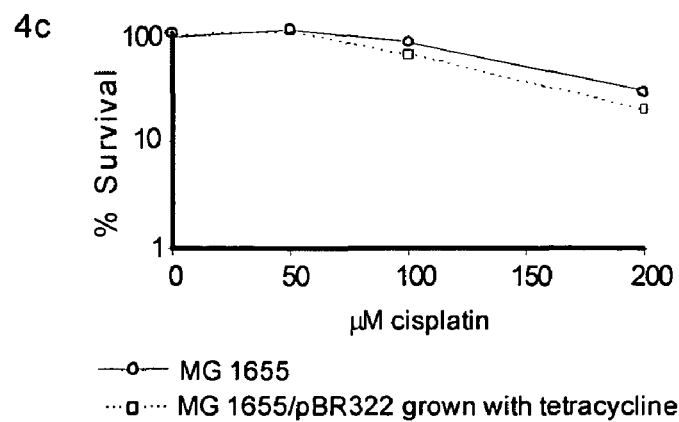

Figure 5

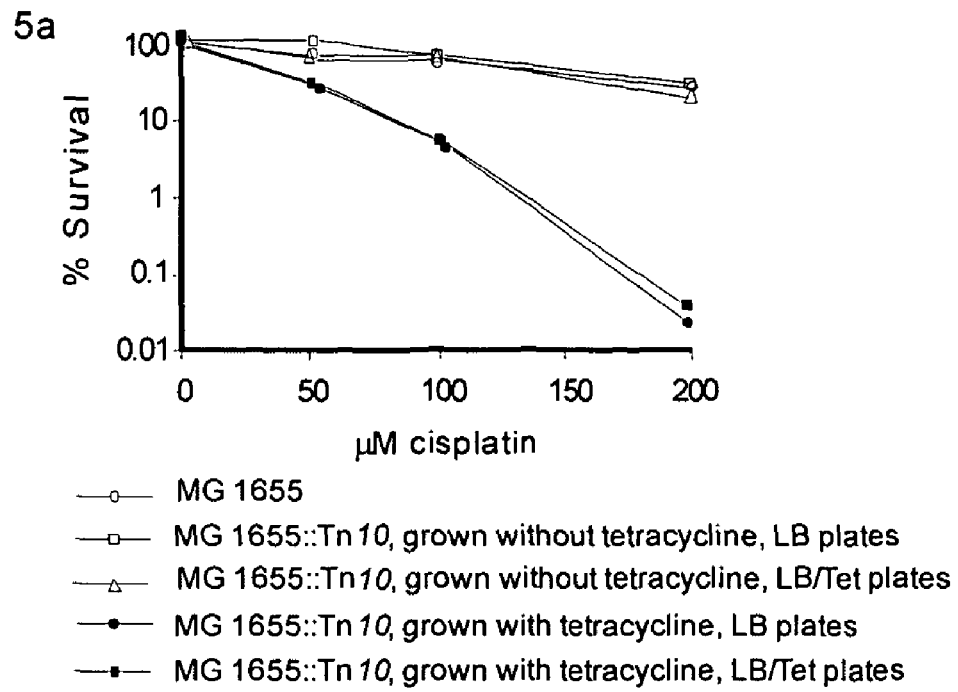

5a

— ○ — MG 1655
— □ — MG 1655::Tn10, grown without tetracycline, LB plates
— △ — MG 1655::Tn10, grown without tetracycline, LB/Tet plates
— ● — MG 1655::Tn10, grown with tetracycline, LB plates
— ■ — MG 1655::Tn10, grown with tetracycline, LB/Tet plates

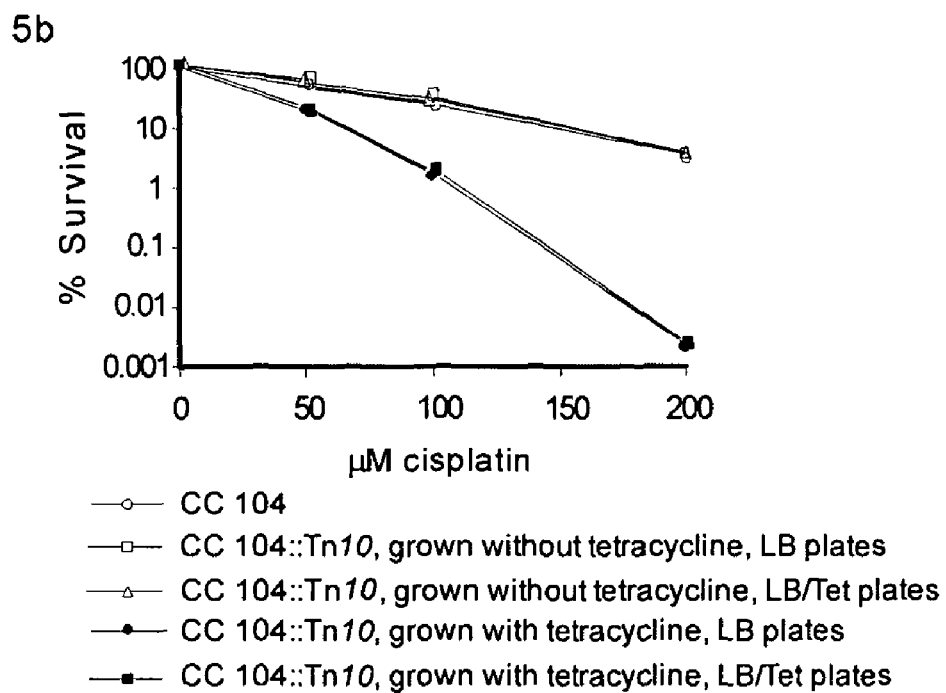

5b

— ○ — CC 104
— □ — CC 104::Tn10, grown without tetracycline, LB plates
— △ — CC 104::Tn10, grown without tetracycline, LB/Tet plates
— ● — CC 104::Tn10, grown with tetracycline, LB plates
— ■ — CC 104::Tn10, grown with tetracycline, LB/Tet plates Figure 6
6a
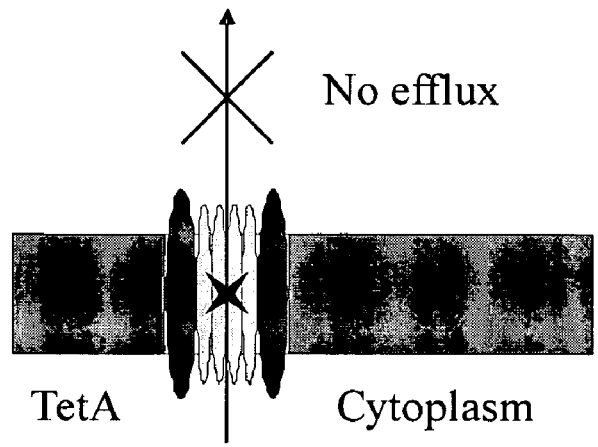
$[Tc-Mg]^+$
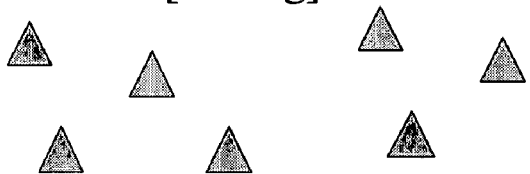
6b
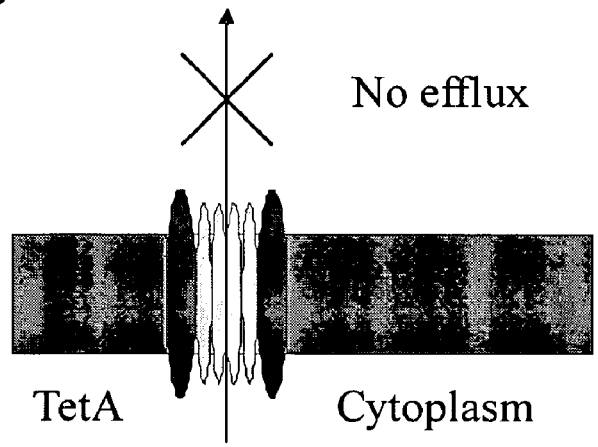
$[Tc-Mg-Pt]$

Figure 7
7a
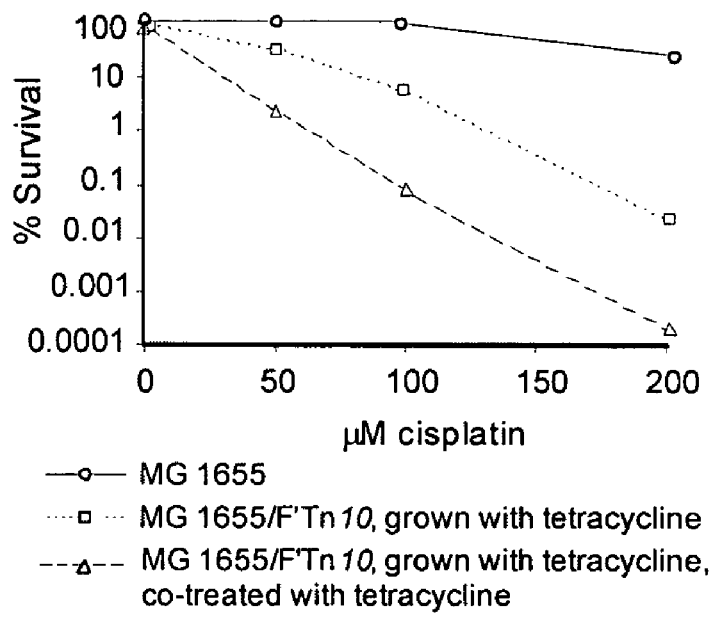
—○— MG 1655
····□···· MG 1655/F'Tn*10*, grown with tetracycline
--△-- MG 1655/F'Tn*10*, grown with tetracycline, co-treated with tetracycline
7b
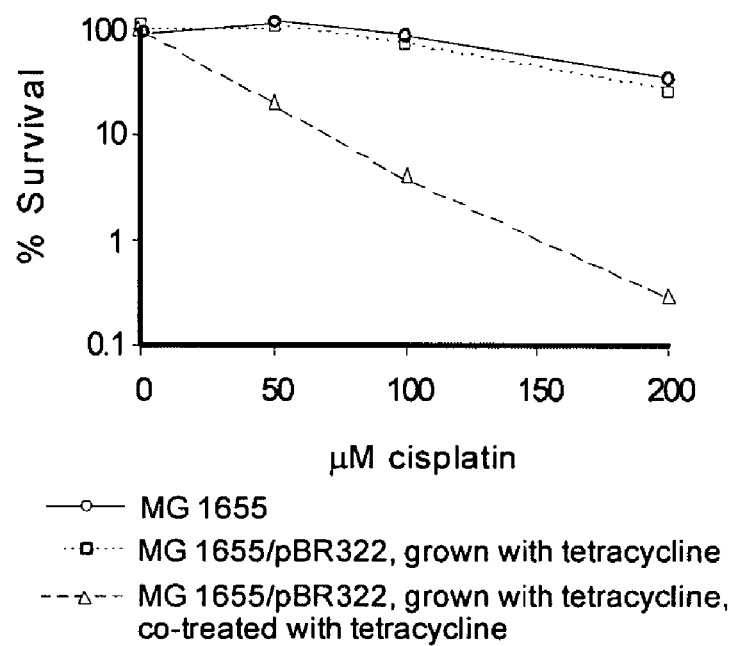
—○— MG 1655
····□···· MG 1655/pBR322, grown with tetracycline
--△-- MG 1655/pBR322, grown with tetracycline, co-treated with tetracycline

Figure 8
8a
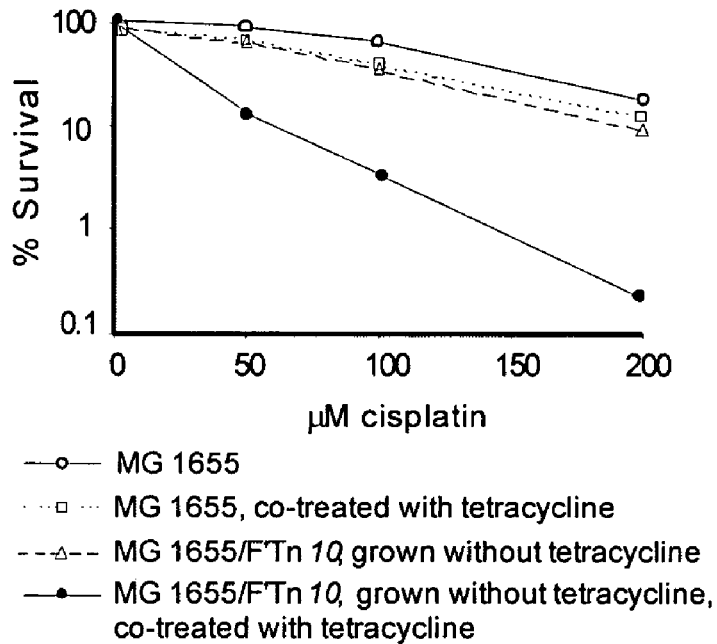
—o— MG 1655
···□··· MG 1655, co-treated with tetracycline
--△-- MG 1655/F'Tn 10, grown without tetracycline
—●— MG 1655/F'Tn 10, grown without tetracycline, co-treated with tetracycline
8b
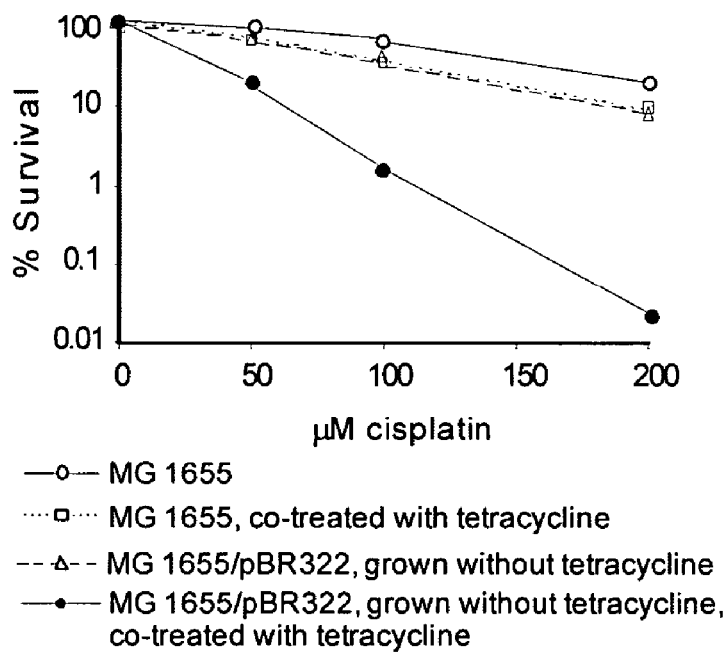
—o— MG 1655
···□··· MG 1655, co-treated with tetracycline
--△-- MG 1655/pBR322, grown without tetracycline
—●— MG 1655/pBR322, grown without tetracycline, co-treated with tetracycline Figure 9
9a
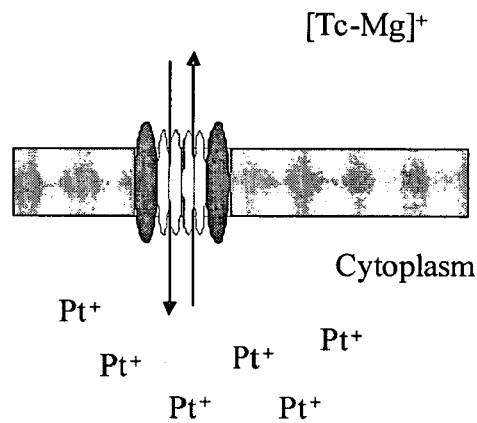
9b
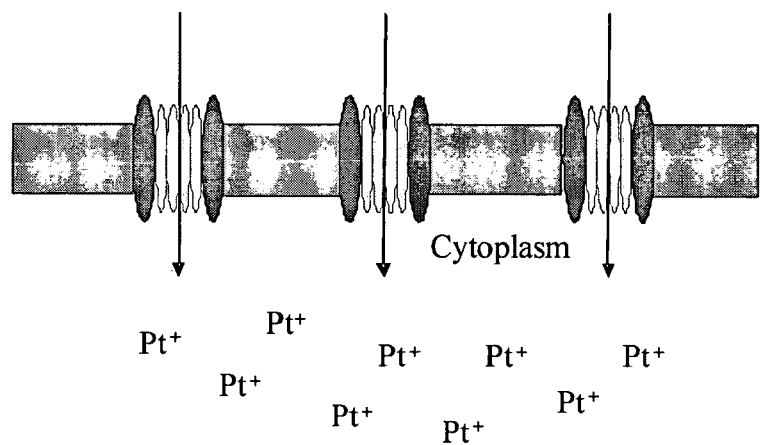
9c
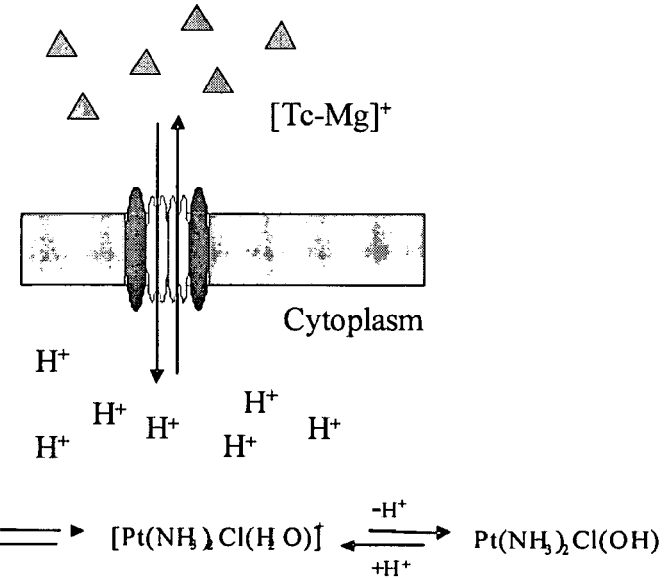

Figure 9 (continued)
9d
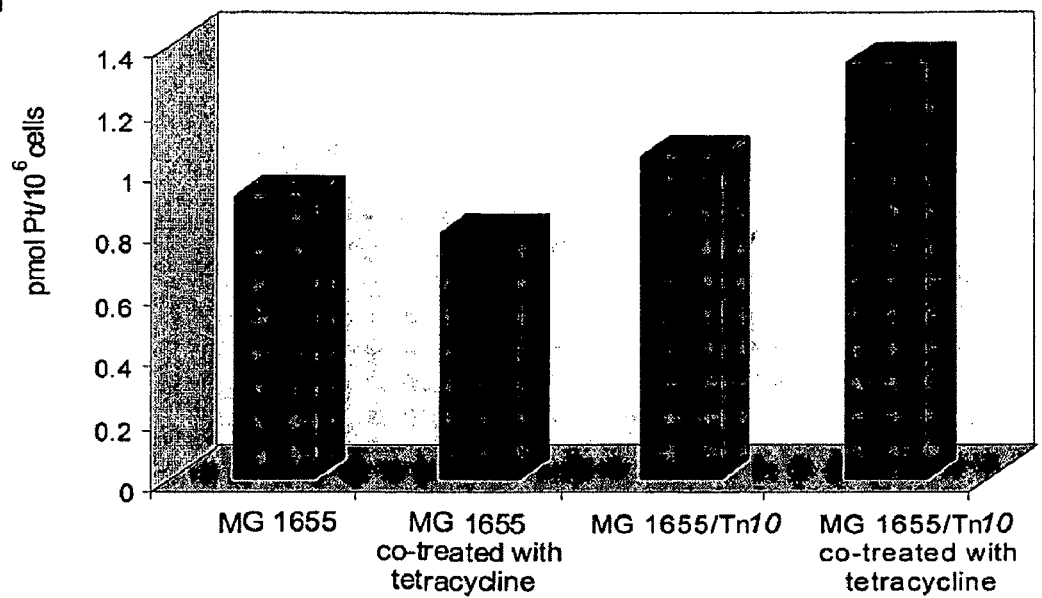
9e
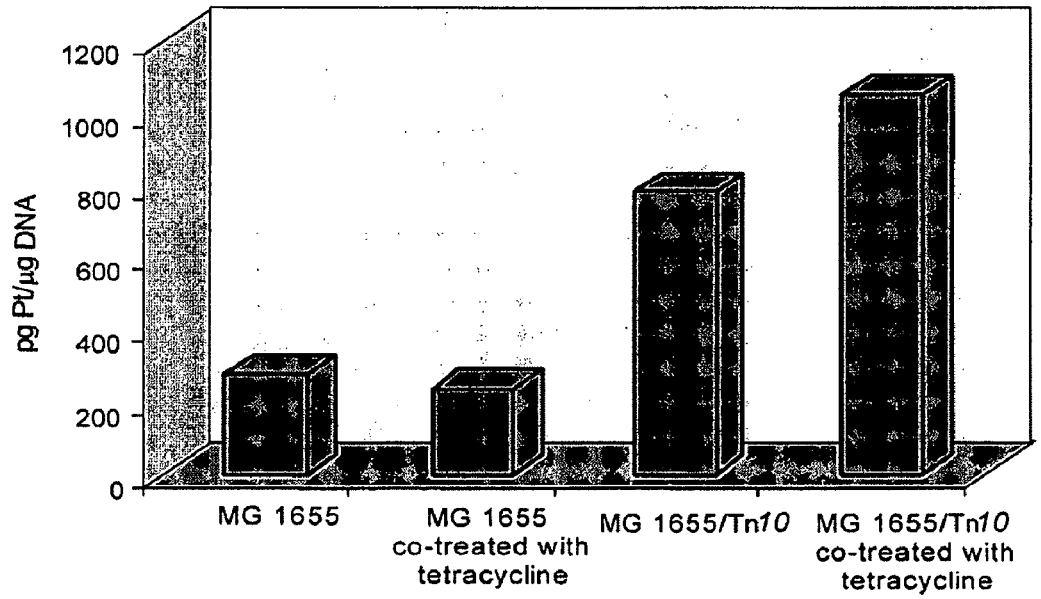

—○— MG 1655

···□··· MG 1655, co-treated with tetracycline

--△-- MG1655/F'Tn*10*, grown without tetracycline

—●— MG1655/F'Tn*10*, grown without tetracycline, co-treated with tetracycline

···■··· MG 1655/F'Tn*10*, grown with tetracycline

--▲-- MG 1655/F'Tn *10* grown with tetracycline, co-treated with tetracycline

US 7,943,600 B2

ANTIMICROBIAL COMBINATION THERAPY

RELATED APPLICATIONS

This application claims benefit under 35 U.S.C. 119(e) of the filing date of U.S. Ser. No. 60/637,790 filed on Dec. 20, 2004, the entire disclosure of which is incorporated herein by reference.

FEDERALLY SPONSORED RESEARCH

This invention was made with government support awarded by the National Institute of Health under Grant Nos. 5-R01-CA86061-04, 5-T32-CA09112-29, and RO1-GM063790. The government has certain rights in this invention.

FIELD OF INVENTION

The invention relates to methods and pharmaceutical compositions for the treatment of conditions associated with an antibiotic resistant microorganism.

BACKGROUND OF INVENTION

The emergence of bacterial resistance to tetracyclines, a broad class of antibiotics, has led to a decline in their use against infectious diseases. Due to the development of resistance, tetracyclines are no longer used in the treatment of many conditions where they were the drugs of choice. Dozens of bacterial diseases were once treated with tetracyclines, and that number is now reduced to only a handful. In those instances where tetracyclines are still used, or even are currently the drugs of choice, the possibility still exists for rapid development of bacterial resistance to this class of antibiotics. This is an unfortunate turn of events, because tetracyclines are broad-range, inexpensive and safe antibiotics that show good oral absorption. Moreover, the development of tetracycline resistance in some instances may come along with the development of concurrent multiple-antibiotic resistance, and alternative antibiotics also may become ineffective in such cases. Therefore the need for new antimicrobial regimens addressing the problem of antibiotic resistance is acute.

SUMMARY OF THE INVENTION

Aspects of the invention relate to antimicrobial compositions and methods. Aspects of the invention are based, in part, on the discovery that the effectiveness of certain toxic compounds (e.g., alkylating agents, and/or nucleic acid damaging agents, and/or heavy metal containing compounds, and/or chelating agents or complex forming compounds) against drug-resistant microbial cells is greater in the presence of an antimicrobial agent. In one embodiment, the effectiveness of a toxic compound may be greater in the presence of an antimicrobial agent that the microbial cells are resistant to. Accordingly, certain antimicrobial agents may sensitize a drug-resistant microorganism to the effects of one or more toxic compounds.

Aspects of the invention relate to synergistic effects obtained when one or more antimicrobial agents are combined with one or more toxic compounds. Aspects of the invention also relate to synergistic combinations of antimicrobial agents and toxic compounds. As used herein, synergistic refers to a therapeutic effect greater than the therapeutic effect of either agent or compound used alone. In one embodiment, aspects of the invention include combinations of one or more antimicrobial agents with one or more nucleic acid damaging agents (e.g. DNA damaging agents). In another embodiment, aspects of the invention include combinations of one or more antimicrobial agents with one or more alkylating agents. In a further embodiment, aspects of the invention include combinations of one or more antimicrobial agents with one or more heavy metal containing compounds (e.g., heavy metal salts). In yet another embodiment, aspects of the invention include combinations of one or more antimicrobial agents with one or more chelating agents or complex forming compounds. It should be appreciated that aspects of the invention relate to combinations of two or more different types of toxic agents along with one or more antimicrobial agents. Antimicrobial agents may be antibiotics (e.g., cytostatic antibiotics or cytotoxic antibiotics). In one embodiment, combinations of the invention may be provided for therapeutic use.

Aspects of the invention also relate to antimicrobial methods. In one embodiment, aspects of the invention include methods for preventing microbial growth. In another embodiment, aspects of the invention include methods for stopping microbial growth. In a further embodiment, aspects of the invention include methods for killing microbial cells. Methods of the invention can be performed in vivo, ex vivo, in vitro, etc. Methods of the invention may be particularly useful to kill or inhibit (e.g., to prevent or stop the growth of) drug-resistant microbial cells (e.g., antibiotic-resistant microbial cells). Methods and compositions of the invention may be particularly useful for killing or inhibiting drug-resistant microbial cells using low doses of certain toxic compounds. In other embodiments, combinations of the invention may be useful for killing or inhibiting drug-resistant microbial cells using low doses of certain antimicrobial agents.

Aspects of the invention also relate to treating a subject having a disease associated with a microbial infection. In one embodiment, aspects of the invention include treating a drug-resistant microbial infection (e.g., an antibiotic-resistant microbial infection) by administering, to an infected subject, a therapeutic combination of an antimicrobial agent along with a toxic compound. Methods and composition of the invention may be particularly useful for treating drug-resistant microbial infections using low doses of certain toxic compounds.

Aspects of the invention also relate to sterilizing devices and/or compositions to prevent microbial contamination. In one embodiment, medical and/or dental equipment, devices, and/or compositions may be sterilized using a combination of one or more antimicrobial agents and one or more toxic compounds according to methods of the invention. In another embodiment, methods of the invention may be useful for sterilizing facilities at medical and/or dental centers (e.g., hospital rooms, operating rooms, emergency rooms, etc.).

BRIEF DESCRIPTION OF THE DRAWINGS

FIG. 1 shows (a) the chemical structures of tetracycline and cisplatin and (b) a schematic depicting the induction of Tn10 tetracycline resistance determinant by tetracycline.

FIG. 2 is a graph that shows the survival of MG1655/F'Tn10::tet and MG1655/F'Tn10::kan respectively, grown in the presence and in the absence of (a) tetracycline, (b) kanamycin in the growth medium.

FIG. 4 is a graph that shows the survival of (a) AB1157/pBR322, grown with tetracycline; (b) CC104/pBR322, grown with tetracycline; (c) MG1655/pBR322, grown with tetracycline.

FIG. 5 is a graph that shows the post-treatment with tetracycline does not affect survival of Tn10 carrying cells. (a) Survival of MG1655/F'Tn10, grown with and without tetracycline and plated on LB and LB/Tet plates. (b) Survival of CC104 mutY::tet, grown with and without tetracycline and plated on LB and LB/Tet plates.

FIG. 7 is a graph that shows the survival of tetracycline-resistant cells, grown with tetracycline and either treated with cisplatin alone, or co-treated with cisplatin in the presence of tetracycline. (a) MG1655/F'Tn10. (b) MG1655/pBR322.

FIG. 8 is a graph that shows the survival of tetracycline-resistant cells, grown without tetracycline and either treated with cisplatin alone, or co-treated with cisplatin in the presence of tetracycline. (a) MG1655/F'Tn10. (b) MG1655/pBR322.

FIG. 9 is (a-c) a schematic depicting possible mechanisms of cisplatin toxicity in tetracycline resistant bacteria, (d) a bar graph that shows the total cellular platinum levels in MG1655 and MG1655/F'Tn10, as determined by atomic absorption spectroscopy, (e) a bar graph that shows the DNA platinum levels in MG1655 and MG1655/F'Tn10, as determined by atomic absorption spectroscopy.

DETAILED DESCRIPTION OF THE INVENTION

Figure 3:
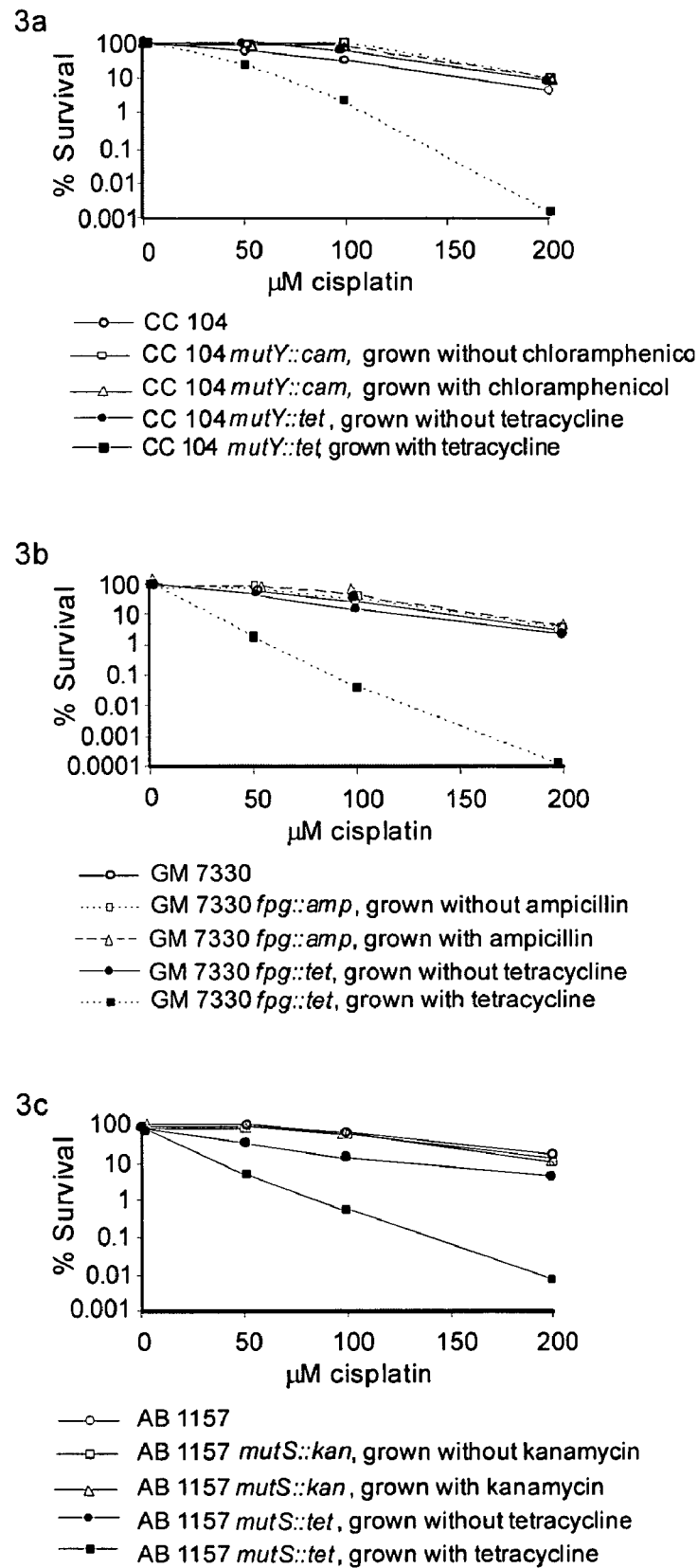
FIG. 3 is a graph that shows (a) survival of CC104, CC104 mutY::cam, grown with and without chloramphenicol, and CC104 mutY:: tet, grown with and without tetracycline. (b) survival of GM7330, GM7330 fpg::amp, grown with and without ampicillin, and GM7330 fpg::tet, grown with and without tetracycline. (c) survival of AB1157, AB1157 mutS::kan, grown with and without kanamycin, and AB1157 mutS::tet, grown with and without tetracycline.

According to aspects of the invention, a microorganism that is resistant to an antimicrobial agent (e.g., tetracycline or an analog thereof) may be killed or inhibited by certain toxic compounds (e.g., cisplatin or an analog thereof) in the presence of the antimicrobial agent. In one embodiment, a drug-resistant microorganism may be more sensitive to certain compounds when the drug-resistant microorganism is exposed to one or more of the drugs that the microorganism is resistant to. Accordingly, the drug-resistant microorganism may be contacted with certain toxic compounds along with the antimicrobial agent(s). In one embodiment, the drug-resistant microorganism may be contacted with the antimicrobial agent(s) before being contacted with the toxic compound(s). In one embodiment, the antimicrobial agent(s) may be removed before or at the same time that the toxic compound(s) is (are) introduced. However, the presence of the antimicrobial agent(s) may be maintained along with the toxic compound(s). In a further embodiment, the antimicrobial agent(s) may be introduced after the toxic compound(s).

Accordingly, a subject infected with a microbial organism may be treated with a combination of an antimicrobial agent and a toxic compound. In one embodiment, the antimicrobial agent may be administered prior to the toxic compound. The antimicrobial agent also may be administered during the time that the toxic compound is being administered.

In one embodiment, a tetracycline resistant microorganism (e.g., a tetracycline resistant bacterium) is selectively susceptible to killing by a toxic compound in the presence of tetracycline or a tetracycline analog. For example, bacteria expressing a tetracycline resistance gene are selectively susceptible to killing by the DNA-damaging drug cisplatin in the presence of tetracycline. Bactria that are not expressing the gene for tetracycline resistance may not be affected by the treatment. Tetracycline-resistant bacteria grown in tetracycline and subsequently treated with cisplatin in the presence of tetracycline were killed about $10^5$ fold more effectively than wild-type bacteria, or than bacteria that were tetracycline resistant but not exposed to tetracycline. This effect may be achieved with low doses of cisplatin (e.g., including from about 5 μM to about 20 μM). Such doses of cisplatin may be used therapeutically in vivo and are lower than certain cisplatin doses that are currently used for cancer therapy. Accordingly, aspects of the invention may be useful for treating microbial infections using low levels of toxic compounds thereby minimizing or avoiding side-effects associated with the toxic compounds. However, aspects of the invention also relate to higher or lower doses of cisplatin.

Accordingly, in one embodiment, a subject having a condition associated with a drug-resistant microbial infection (e.g., an infection by a microorganism that is resistant to at least a first drug) may be treated by administering a therapeutically effective combination of the first drug (e.g., an antibiotic) and a DNA damaging agent. Similarly, a subject having a condition associated with the drug-resistant microbial infection (e.g., a drug-resistant bacterial infection) may be treated by administering a therapeutically effective combination of the first drug and an alkylating agent. In one embodiment, the effectiveness of the toxic compound may be enhanced if the antimicrobial drug is administered prior to administering the toxic compound. In one embodiment, an antimicrobial agent is administered prior to administering the toxic compound, and treatment with the antimicrobial agent is continued after the toxic compound is provided.

It should be appreciated that aspects of the invention described herein include administering two or more microbial agents in combination with one or more toxic compounds. Aspects of the invention also include administering two or more toxic compounds in combination with one or more antimicrobial agents. Accordingly, when a method or composition is described in the context of "an antimicrobial agent" or "toxic compound" it should be understood to mean at least one antimicrobial agent or at least one toxic compound unless expressly limited to a single antimicrobial agent or toxic compound.

It also should be appreciated that in one embodiment, a method for administering a combination of an antimicrobial agent and a toxic compound may involve administering the antimicrobial agent and the toxic compound separately, but to the same subject. As discussed herein, the antimicrobial agent may be administered to a subject before and/or along with the toxic compound. However, in another embodiment, a single composition or treatment may be an antimicrobial agent prepared in a composition comprising a toxic compound. Accordingly, administration of the combination composition results in administration of both the antimicrobial agent and the toxic compound. In a further embodiment, a subject may be treated with an antimicrobial agent alone for a first period of time followed by treatment with a composition that includes both the antimicrobial agent and a toxic compound.

In one aspect, embodiments of the invention include administering an antimicrobial agent for about one hour, about one day, about one week, or about one month before administering a toxic compound or a combination of a toxic compound and antimicrobial agent. However, this time period may be shorter, longer, or of intermediate duration.

In one embodiment, a subject may be treated with a toxic compound when the presence of a drug-resistant infection is suspected or has been diagnosed or detected. An infected subject may have been treated unsuccessfully with one or more antimicrobial agents. In this case, the administration of a low level of a toxic compound may be effective to kill or inhibit the infection. In one embodiment, treatment with the antimicrobial agent is continued during the administration of the toxic compound. In one embodiment, the administration of the antimicrobial agent is prior to or subsequent to the administration of the toxic compound.

In one embodiment, aspects of the invention include treating a subject with a combination of an antimicrobial agent and a toxic compound before a drug-resistant infection is suspected, diagnosed, or detected. In one embodiment, no infection is known to be present. However, the combination may be administered to prevent an infection. In another embodiment, an infection is present, but the infection is not known to be drug-resistant. These applications may be useful in the context of a surgical operation to prevent an infection or to prevent the development of a drug-resistant infection. These applications also may be useful in the context of a known risk of infection in order to prevent the infection (e.g., a drug-resistant infection) or to treat an early asymptomatic infection (e.g., a drug-resistant microorganism in the early stages of infection). A known risk of infection may include the presence of infected individuals within a population (e.g., a meningitis outbreak in a population); known exposure or suspected exposure to one or more biological warfare agents (e.g., a drug-resistant microbial agent used as a biological weapon); an immuno-compromised subject; cancer subject; subject with burns; and other risk factors; or any combination of two or more of the above.

It should be appreciated that aspects of the invention may be useful for killing or inhibiting multi-drug-resistant microorganisms. Accordingly aspects of the invention may be useful for treating multi-drug-resistant microbial infections. In certain embodiments where multi-drug resistance is associated with a common mechanism (e.g., an efflux pump), any one or more of the drugs that the organism is resistant to may be combined with a toxic compound as described herein.

Although not wishing to be bound by theory, a proposed molecular mechanism of certain aspects of the invention may involve increased activity of the toxic compound. For example, in the case of cisplatin, increased cisplatin reactivity and amount of DNA damage may be due to changes in the cellular environment, such as pH, and by the induction of tetracycline resistance (e.g., tetracycline pump antiporter activity.) Alternatively, and not exclusively, the molecular mechanism of certain compositions of the invention may involve one or more of the following: Tet repressor hijacking by cellular lesions caused by toxic compounds (e.g., cisplatin-DNA adducts), enhanced uptake of toxic compounds by the tetracycline resistant bacteria, enhanced cytotoxicity of the toxic compounds in the cellar environment of the tetracycline resistant bacteria, and interference of the cytotoxic compounds with tetracycline antiporter activity either by blocking the antiporter directly or by interfering with tetracycline-$Mg^{2+}$ chelation. Accordingly, any antibiotic for which resistance is mediated by any of the above mechanisms can be used in therapeutic combinations of the invention.

Toxic Compounds

In one embodiment, a toxic compound of the invention may be a nucleic acid damaging agent (e.g., DNA-damaging agent). Nucleic acid damaging agents of the invention can be platinum compounds, other DNA damaging agents such as various alkylators of DNA, N-methyl-N'-nitro-N-nitrosoguanidine (MNNG), methylmethane sulfonate (MMS), mitomycin C, streptozotocin, bleomycin, etc., or any combination of two or more thereof. Platinum DNA damaging compounds are well known in the art and they may be cisplatin (cis-diamminedichloroplatinum(II)), trans-diamminedichloroplatinum(II), carboplatin, cis-ethylenediammine dichloroplatinum(II), oxaliplatin (trans-R,R-diamminocyclohexaneoxalatoplatinum(II)), 1,2-diamminocyclohexaneoxalatoplatinum(II), or any combination of two or more thereof.

In one embodiment, a toxic compound of the invention may be an alkylating agent.

In one embodiment, a toxic compound of the invention may be a heavy metal containing compound, including, but not limited to, a heavy metal salt. A heavy metal containing compound of the invention may include Pt, Ni, Cd, Hg, Pb, Ag, Tl, or any other heavy-metal, or any combination thereof. Accordingly, a toxic compound may include a salt of any one or more these heavy metals.

In one embodiment, a toxic compound of the invention may be a chelating agent/complex-forming compound. A chelating agent/complex forming compound may be fusaric acid; quinaldic acid; 8-hydroxyquinoline; 1,10-phenanthroline; 2,2'-bypiridine; 5-thenoyltrifluoroacetone (TTA); ethylenediamine tetraacetic acid (EDTA); ethylenediamine di(o-hydroxy-phenyl acetic acid) (EDDA); picolinic acid; quinolinic acid; pyrithione; anthranilic acid; picolinic acid oxide; pyrrole-2-carboxylic acid; nicotinic acid; any other chelating agent/complex forming compound; or a combination thereof.

In one embodiment, radiation (e.g., UV-radiation, gamma radiation, or any other form of radiation) may be substituted for, or used in addition to, a toxic compound.

It should be appreciated that aspects of the invention may include two or more of the above toxic compounds. Also, certain nucleic acid damaging agents may be alkylating agents. Similarly, certain alkylating agents may be nucleic acid damaging agents.

In one embodiment, a toxic compound may be activated or rendered more potent (e.g., more alkylating or more damaging to nucleic acid) inside a microorganism when it is exposed to an antimicrobial agent that causes physiological changes in the microorganism (e.g., changes in internal salt concentrations, pH). In one embodiment, a toxic compound may be activated or rendered more potent when exposed to a drug-resistant microorganism in combination with an antimicrobial agent, if the antimicrobial agent causes physiological changes to a drug-resistant microorganism (as opposed to a normal drug-sensitive microorganism).

According to aspects of the invention, a toxic compound may be administered to a subject in low doses to treat a microbial infection when combined with an antimicrobial agent that sensitizes the microorganism to the toxic compound. In one embodiment, low doses of a toxic compound may be particularly effective to treat a drug-resistant microbial infection. In one embodiment, a toxic compound may be administered to a subject at a dose of between 10 mg/m$^2$ and 100 mg/m$^2$, including between 20 mg/m$^2$ and 80 mg/m$^2$. In certain embodiments, a toxic compound may be administered at lower than 50 mg/m$^2$, or lower than 25 mg/m$^2$, or lower than 10 mg/m$^2$, or lower than 5 mg/m$^2$, or lower than 1 mg/m$^2$, or lower than 0.5 mg/m$^2$, or lower than 0.1 mg/m$^2$. A human female is approximately 1.6 m and a human male is approximately 2.0 m$^2$. In one embodiment, a toxic compound is administered to a human or other mammal at a dose that results in a blood concentration of less than 100 µM, or less than 50 µM, or less than 25 µM, or less than 10 µM, or less than 5 µM, or less than 1 µM, or less than 0.5 µM, or less than 0.1 µM.

Antimicrobial Agents

In one embodiment, compositions and methods of the invention include an antimicrobial agent for sensitizing a microorganism to a toxic compound. In one embodiment, the microorganism is resistant to the antimicrobial agent. The antimicrobial agent may enhance the uptake of a toxic compound by a microorganism. The antimicrobial agent may enhance the uptake of a toxic compound by a drug-resistant microorganism (e.g., a microorganism that is resistant to the antimicrobial agent). The antimicrobial agent may alter the physiology of the microorganism in a manner and to an extent that activates a toxic compound that contacts (e.g., is taken up by) the microorganism. The antimicrobial agent may alter the physiology of a drug-resistant microorganism resulting in a toxic compound being activated when it contacts the drug-resistant microorganism. However, in some embodiments the microorganism may be resistant to two or more antimicrobial agents that are used along with one or more toxic compounds.

In another embodiment, compositions and methods of the invention also include a second antimicrobial agent. The microorganism may not be resistant to the second antimicrobial agent. However, the second antimicrobial agent may be useful further to kill or inhibit the microorganism.

In certain embodiments of the invention, the microorganism is resistant to an antibiotic that has the same mode of action as tetracycline, e.g. inhibition of protein synthesis. In another embodiment the microorganism is resistant to an antibiotic that shares the some of the properties of tetracycline and the resistance is induced and/or affected by: a change of the intracellular environment, an efflux pump, complex-forming, metal-binding, and/or transcriptional induction or any combination thereof. In one embodiment, a combination of any antibiotic and a toxic compound may be used if the microorganism is resistant to the antibiotic via a mechanism that is mediated by: a change of the intracellular environment, an efflux pump, complex-forming, metal-binding, and/or transcriptional induction or any combination thereof.

In one embodiment, an antimicrobial agent may be tetracycline or an analog thereof. Tetracycline is a bacteriostatic agent that stops bacterial growth by reversibly binding to the ribosome and inhibiting protein synthesis. Currently, three types of tetracycline resistance are known: active efflux of the drug, ribosome protection, and chemical modification of tetracycline. However, only the first two are of clinical significance (Schnappinger and Hillen, 1996; Chopra and Roberts, 2001). Active efflux of drug is the most common tetracycline resistance mechanism, mediated by expression of tetracycline-specific trans-membrane efflux pumps. In Gram-negative bacteria, there are currently several known classes of tetracycline resistance determinants encoding tetracycline efflux pumps which share a common genetic organization (Roberts, 1996; Butaye et al, 2003). The most widespread and the best-studied tetracycline resistance determinant of Gram-negative bacteria is the class B determinant associated with transposon Tn10 (Hillen and Berens, 1994). It consists of two genes in a divergent orientation, one coding for TetR, the tetracycline-responsive repressor protein, and another coding for TetA efflux pump protein—an antiporter which counterbalances the export of [tetracycline-Mg]$^+$ complex out of the cell with the import of a single H$^+$. These two genes share a central regulatory region, with two overlapping tet promoters and operators. In the absence of tetracycline, TetR protein binds to each of the two tet operators, and blocks transcription of both tetR and tetA genes. However, when tetracycline is present, it induces a conformational change in the TetR repressor protein by binding it in a complex with Mg$^{2+}$. The conformational change in TetR induced by the [tetracycline-Mg]$^+$ complex results in dissociation of the repressor protein from the operator DNA. This leads to expression of both TetR and TetA proteins, ensuring the efficient export of tetracycline before it can reach its target, the ribosome (Kisker et al, 1995; Orth et al, 1998; Orth et al, 2000; Saenger et al, 2000).

Tetracyclines were discovered in the late 1940s. Tetracyclines quickly became widely used because of their multiple important advantages. The cost of production of tetracyclines is low, they are safe, and can be taken orally. Tetracyclines are active against a broad range of traditional Gram-negative and Gram-positive bacterial pathogens, as well as against bacteria lacking cell walls and those found intracellularly (such as mycoplasmas, chlamydiae, and rickettsiae). They are also used against some eukaryotic protozoan parasites, such as *Toxoplasma gondii, Giardia lamblia, Plasmodium falciparum, Entamoeba histolytica, Leishmania major*, and *Trichomonas vaginalis*.

A significant aspect of the therapeutic applicability of tetracyclines is that they are the agents primarily employed against bacteria that have high potential for use in bacterial biological weapons. Three pathogenic organisms that are most likely to be involved as biological weapons are *Yersinia pestis* (plague), *Bacillus anthracis* (anthrax), and *Francisella tularensis* (tularemia); Tetracyclines are antibiotics of choice for treatment and prophylaxis in each case.

However, the emergence of bacterial resistance to tetracyclines became a serious problem limiting their use in clinical practice. Today, most genera examined have tetracycline-resistant isolates, although the percentage varies according to genus and species and geographic location. Due to the emergence of resistance, tetracyclines are no longer antibiotics of choice in the treatment of many conditions. For example, although tetracyclines were extensively used in the treatment of bacterial respiratory infections, resistance as well as availability of alternative drugs resulted in a decline in use of tetracyclines in the treatment of pneumonia, where tetracyclines have long been drugs of choice.

Despite the wide spread emergence of resistance in many instances, tetracyclines are still used in the treatment of a variety of bacterial and non-bacterial infections. There are a number of conditions where tetracyclines still are first-line antibiotics. Tetracyclines are used extensively against rickettsial infections: typhus, scrub typhus, and spotted fevers, including Mediterranean spotted fever, Rocky Mountain spotted fever, and Q fever. A major area of clinical use of tetracyclines is the treatment of acne. Periodontal disease is another area of extensive use. Tetracyclines also are widely used in the treatment of genito-urinary infections, and some bacterial gastro-intestinal infections, for example, cholera. Some rare conditions for which tetracycline may be used are plague and tularemia.

Some applications of tetracyclines are quite recent. For example, tetracyclines are among the first-choice antibiotics against Lyme disease, which is the most common tick-borne infection in the United States. They are also used for relapsing fever caused by *Borrelia recurrentis*, also a tick-borne infection. Some studies show that tetracyclines may be effective against leprosy. Gastritis and peptic ulcer disease associated with *Helicobacter pylori* have also been recently treated with tetracyclines. Another important new application of tetracycline is prophylaxis and treatment of malaria caused by *Plasmodium falciparum*, a eukaryotic parasite. Even mefloquine-resistant malaria at this time is responsive to tetracycline therapy, and tetracycline is currently the drug of choice. Also, activity of tetracyclines against filarial nematodes has recently been demonstrated, and it is possible that nematode-related diseases will be treatable by tetracycline in the future.

Tetracycline analogs include minocycline, doxycycline, oxytetracycline, demethylchlortetracycline, methacycline, and chlortetracycline. Tetracycline and tetracycline analogs may be provided in any form including powders, salts, solutions, etc. (including tetracycline HCl which may be prepared in an appropriate solution or buffer.)

Tetracycline and tetracycline analogs may be used at between 10 and 1000 mg/day, or about 100 mg/day, or 200 mg/day, or 300 mg/day, or 500 mg/day and may be used in concentrations between 1 and 100 µg/ml, or between 10 and 50 µg/ml, or at any other suitable concentration (e.g., at about 5, or 10, or 15, or 20, or 25, or 30, or 35, or 40, or 45, or 50 µg/ml, etc.). Lower concentrations of tetracycline may be more appropriate when used with a toxic compound for which there is a strong synergistic effect (e.g., cisplatin). Similarly, other antimicrobial agents may be used in any of the concentrations described herein.

In one embodiment, aspects of the invention include one or more other antibacterial agents (e.g., antibiotics) with or without tetracycline. Antibacterial agents kill or inhibit the growth or function of bacteria. A large class of antibacterial agents includes antibiotics. Antibiotics that are effective for killing or inhibiting a wide range of bacteria are referred to as broad spectrum antibiotics. Other types of antibiotics are predominantly effective against only Gram-positive or Gram-negative bacteria. These types of antibiotics are referred to as narrow spectrum antibiotics. Other antibiotics that are effective against a single organism or disease and not against other types of bacteria are referred to as limited spectrum antibiotics.

Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors. Cell wall synthesis inhibitors inhibit a step in the process of cell wall synthesis, and in general in the synthesis of bacterial peptidoglycan. Cell wall synthesis inhibitors may be β-lactam antibiotics, natural penicillins, semi-synthetic penicillins, ampicillin, clavulanic acid, cephalolsporins, or bacitracin.

The β-lactams are antibiotics containing a four-membered β-lactam ring which inhibits the last step of peptidoglycan synthesis. β-lactam antibiotics can be synthetic or natural. The natural antibiotics are generally produced by two groups of fungi, *Penicillium* and *Cephalosporium* molds. The β-lactam antibiotics produced by *Penicillium* are the natural penicillins, such as penicillin G or penicillin V. These are produced by fermentation of *Penicillium chrysogenum*. The natural penicillins have a narrow spectrum of activity and are generally effective against *Streptococcus, Gonococcus,* and *Staphylococcus*. Other types of natural penicillins, which are also effective against Gram-positive bacteria, include penicillins F, X, K, and O. However, they may be used against other organisms.

Semi-synthetic penicillin are generally modifications of the molecule 6-aminopenicillanic acid produced by a mold. The 6-aminopenicillanic acid can be modified by addition of side chains which produce penicillins having broader spectrums of activity than natural penicillins or various other advantageous properties. Some types of semi-synthetic penicillins have broad spectrums against Gram-positive and Gram-negative bacteria, but are inactivated by penicillinase. These semi-synthetic penicillins include ampicillin, carbenicillin, oxacillin, azlocillin, mezlocillin, and piperacillin. Other types of semi-synthetic penicillins have narrower activities against Gram-positive bacteria, but have developed properties such that they are not inactivated by penicillinase. These include, for instance, methicillin, dicloxacillin, and nafcillin. Some of the broad spectrum semi-synthetic penicillins can be used in combination with β-lactamase inhibitors, such as clavulanic acids and sulbactam. The β-lactamase inhibitors do not have anti-microbial action but they function to inhibit penicillinase, thus protecting the semi-synthetic penicillin from degradation.

Another type of β-lactam antibiotic includes the cephalosporins. Cephalosporins are produced by *Cephalosporium* molds, and have a similar mode of action to penicillin. They are sensitive to degradation by bacterial β-lactamases, and thus, are not always effective alone. Cephalolsporins, however, are resistant to penicillinase. They are effective against a variety of Gram-positive and Gram-negative bacteria. Cephalolsporins include, but are not limited to, cephalothin, cephapirin, cephalexin, cefamandole, cefaclor, cefazolin, cefuroxine, cefoxitin, cefotaxime, cefsulodin, cefetamet, cefixime, ceftriaxone, cefoperazone, ceftazidine, and moxalactam.

Bacitracin belongs to another class of antibiotics which inhibit cell wall synthesis. These antibiotics, produced by *Bacillus* species, prevent cell wall growth by inhibiting the release of muropeptide subunits or peptidoglycan from the molecule that delivers the subunit to the outside of the membrane. Although bacitracin is effective against Gram-positive bacteria, its use is limited in general to topical administration because of its high toxicity.

Carbapenems are another type of broad spectrum β-lactam antibiotic capable of inhibiting cell wall synthesis. Examples of carbapenems include, but are not limited to, imipenems. Monobactems are also broad spectrum β-lactam antibiotics, and include, euztreonam. An antibiotic produced by *Streptomyces*, vancomycin, is also effective against Gram-positive bacteria by inhibiting cell membrane synthesis.

Another class of anti-bacterial agents includes the antibacterial agents that are cell membrane inhibitors. These compounds disorganize the structure or inhibit the function of bacterial membranes. Alteration of the cytoplasmic membrane of bacteria results in leakage of cellular materials from the cell. Compounds that inhibit or interfere with the cell membrane cause death of the cell because the integrity of the cytoplasmic and outer membranes is vital to bacteria. One problem with anti-bacterial agents that are cell membrane inhibitors is that they can produce effects in eukaryotic cells as well as bacteria because of the similarities in phospholipids in bacterial and eukaryotic membranes. Thus these compounds are rarely specific enough to permit these compounds to be used systemically and prevent the use of high doses for local administration.

One clinically useful anti-bacterial agent that is a cell membrane inhibitor is Polymyxin, produced by *Bacillus polymyxis*. Polymyxins interfere with membrane function by binding to membrane phospholipids. Polymyxin is effective mainly against Gram-negative bacteria and is generally used in severe *Pseudomonas* infections or *Pseudomonas* infections that are resistant to less toxic antibiotics. It is also used in some limited instances topically. The limited use of this agent is due to the severe side effects associated with systemic administration, such as damage to the kidney and other organs.

Other cell membrane inhibitors include Amphotericin B and Nystatin produced by the bacterium *Streptomyces* which are also anti-fungal agents, used predominantly in the treatment of systemic fungal infections and *Candida* yeast infections respectively. Imidazoles, produced by the bacterium *Streptomyces*, are another class of antibiotic that is a cell membrane inhibitor. Imidazoles are used as bacterial agents as well as anti-fungal agents, e.g., used for treatment of yeast infections, dermatophytic infections, and systemic fungal infections. Imidazoles include but are not limited to clotrimazole, miconazole, ketoconazole, itraconazole, and fluconazole.

Many anti-bacterial agents are protein synthesis inhibitors. These compounds prevent bacteria from synthesizing structural proteins and enzymes and thus cause inhibition of bacterial cell growth or function or cell death. In general these compounds interfere with the processes of transcription or translation. Anti-bacterial agents that block transcription include but are not limited to Rifampins, produced by the bacterium *Streptomyces* and Ethambutol, a synthetic chemical. Rifampins, which inhibit the enzyme RNA polymerase, have a broad spectrum of activity and are effective against Gram-positive and Gram-negative bacteria as well as *Mycobacterium tuberculosis*. Ethambutol is effective against *Mycobacterium tuberculosis*.

Anti-bacterial agents that block translation interfere with bacterial ribosomes to prevent mRNA from being translated into proteins. In general, this class of compounds includes but is not limited to tetracyclines, chloramphenicol, the macrolides (e.g. erythromycin) and the aminoglycosides (e.g. streptomycin).

Some of these compounds bind irreversibly to the 30S ribosomal subunit and cause a misreading of the mRNA, e.g., the aminoglycosides. The aminoglycosides are a class of antibiotics which are produced by the bacterium *Streptomyces*, such as, for instance streptomycin, kanamycin, tobramycin, amikacin, and gentamicin. Aminoglycosides have been used against a wide variety of bacterial infections caused by Gram-positive and Gram-negative bacteria. Streptomycin has been used extensively as a primary drug in the treatment of tuberculosis. Gentamicin is used against many strains of Gram-positive and Gram-negative bacteria, including *Pseudomonas* infections, especially in combination with tobramycin. Kanamycin is used against many Gram-positive bacteria, including penicillin-resistant *Staphylococci*. One side effect of aminoglycosides that has limited their use clinically is that at dosages which are essential for efficacy, prolonged use has been shown to impair kidney function and cause damage to the auditory nerves leading to deafness.

Another type of translation inhibitor anti-bacterial agent is the tetracyclines. The tetracyclines bind reversibly to the 30S ribosomal subunit and interfere with the binding of charged tRNA to the bacterial ribosome. The tetracyclines are a class of antibiotics, produced by the bacterium *Streptomyces*, that are broad-spectrum and are effective against a variety of Gram-positive and Gram-negative bacteria. Examples of tetracyclines include tetracycline, minocycline, doxycycline, and chlortetracycline. They are important for the treatment of many types of bacteria but are particularly important in the treatment of Lyme disease.

Anti-bacterial agents such as the macrolides bind reversibly to the 50S ribosomal subunit and inhibit elongation of the protein by peptidyl transferase or prevent the release of uncharged tRNA from the bacterial ribosome or both. The macrolides contain large lactone rings linked through glycoside bonds with amino sugars. These compounds include erythromycin, roxithromycin, clarithromycin, oleandomycin, and azithromycin. Erythromycin is active against most Gram-positive bacteria, *Neisseria, Legionella* and *Haemophilus*, but not against the Enterobacteriaceae. Lincomycin and clindamycin, which block peptide bond formation during protein synthesis, are used against Gram-positive bacteria.

Another type of translation inhibitor is chloramphenicol. Chloramphenicol binds the 70S ribosome inhibiting the bacterial enzyme peptidyl transferase thereby preventing the growth of the polypeptide chain during protein synthesis. Chloramphenicol can be prepared from *Streptomyces* or produced entirely by chemical synthesis. One serious side effect associated with chloramphenicol is aplastic anemia. Aplastic anemia develops at doses of chloramphenicol which are effective for treating bacteria in a small proportion (1/50,000) of patients. Chloramphenicol which was once a highly prescribed antibiotic is now seldom used as a result of the deaths from anemia. Because of its effectiveness it is still used in life-threatening situations (e.g. typhoid fever).

Some anti-bacterial agents disrupt nucleic acid synthesis or function, e.g., bind to DNA or RNA so that their messages cannot be read. These include but are not limited to quinolones and co-trimoxazole, both synthetic chemicals and rifamycins, a natural or semi-synthetic chemical. The quinolones block bacterial DNA replication by inhibiting the DNA gyrase, the enzyme needed by bacteria to produce their circular DNA. They are broad spectrum and examples include norfloxacin, ciprofloxacin, enoxacin, nalidixic acid and temafloxacin. Nalidixic acid is a bacteriocidal agent that binds to the DNA gyrase enzyme (topoisomerase) which is essential for DNA replication and allows supercoils to be relaxed and reformed, inhibiting DNA gyrase activity. The main use of nalidixic acid is in treatment of lower urinary tract infections (UTI) because it is effective against several types of Gram-negative bacteria such as *E. coli, Enterobacter aerogenes, K. pneumoniae* and *Proteus* species which are common causes of UTI. Co-trimoxazole is a combination of sulfamethoxazole and trimethoprim, which blocks the bacterial synthesis of folic acid needed to make DNA nucleotides. Rifampicin is a derivative of rifamycin that is active against Gram-positive bacteria (including *Mycobacterium tuberculosis* and meningitis caused by *Neisseria meningitidis*) and some Gram-negative bacteria. Rifampicin binds to the beta subunit of the polymerase and blocks the addition of the first nucleotide which is necessary to activate the polymerase, thereby blocking mRNA synthesis.

Another class of anti-bacterial agents includes compounds that function as competitive inhibitors of bacterial enzymes. The competitive inhibitors are mostly all structurally similar to a bacterial growth factor and compete for binding but do not perform the metabolic function in the cell. These compounds include sulfonamides and chemically modified forms of sulfanilamide which have even higher and broader antibacterial activity. The sulfonamides (e.g., gantrisin and trimethoprim) are useful for the treatment of *Streptococcus pneumoniae*, beta-hemolytic *streptococci* and *E. coli*, and have been used in the treatment of uncomplicated UTI caused by *E. coli*, and in the treatment of meningococcal meningitis.

According to aspects of the invention, antimicrobial agents may be administered to humans or other organisms at standard doses used for treating drug sensitive microorganisms. However, higher or lower dosages may be used. In particular, lower doses may be used when the combination of antimicrobial agent(s) and a toxic compound(s) produces a strong synergistic antimicrobial effect. In one embodiment, an antimicrobial agent and/or a toxic compound may be administered at a dose that results in a serum level of less than 100 µg/ml, or less than 75 µg/ml, or less than 50 µg/ml, or less than 25 µg/ml, or less than 10 µg/ml, or less than 5 µg/ml, or less than 1 µg/ml, or less than 0.5 µg/ml, or less than 0.1 µg/ml.
Microorganisms Aspects of the invention may be useful for killing or inhibiting microorganisms, particularly drug-resistant microorganisms. Microorganisms may be prokaryotic or eukaryotic microorganisms.

Eukaryotic microorganisms include, but are not limited to, protozoan parasites, filarial nematodes, and other eukaryotic protozoa, parasites, and nematodes.

Prokaryotic microorganisms may be infectious, virulent, parasitic, symbiotic, etc. Prokaryotic microorganisms may be bacteria, including drug-resistant bacteria (including multi-drug-resistant bacteria). In one embodiment, antibiotic resistant bacteria are tetracycline resistant bacteria. In one certain embodiment, multi-drug resistant bacteria are tetracycline resistant in addition to being resistant against other drugs.

Bacteria are unicellular organisms which multiply asexually by binary fission. They are classified and named based on their morphology, staining reactions, nutrition and metabolic requirements, antigenic structure, chemical composition, and genetic homology. Bacteria can be classified into three groups based on their morphological forms, spherical (*coccus*), straight-rod (*bacillus*) and curved or spiral rod (*vibrio, campylobacter, spirillum*, and *spirochaete*). Bacteria are also more commonly characterized based on their staining reactions into two classes of organisms, Gram-positive and Gram-negative. Gram refers to the method of staining which is commonly performed in microbiology labs. Gram-positive organisms retain the stain following the staining procedure and appear a deep violet color. Gram-negative organisms do not retain the stain but take up the counter-stain and thus appear pink.

Bacteria have two main structural components, a rigid cell wall and protoplast (material enclosed by the cell wall). The protoplast includes cytoplasm and genetic material. Surrounding the protoplast is the cytoplasmic membrane which includes some of the cell respiratory enzymes and is responsible for the permeability of bacteria and transport of many small molecular weight substances. The cell wall surrounding the cytoplasmic membrane and protoplast is composed of mucopeptides which include complex polymers of sugars cross-linked by peptide chains of amino acids. The wall is also composed of polysaccharides and teichoic acids.

Infectious bacteria include, but are not limited to, Gram-negative and Gram-positive bacteria. Gram-positive bacteria include, but are not limited to *Pasteurella* species, *Staphylococci* species, and *Streptococcus* species. Gram-negative bacteria include, but are not limited to, *Escherichia coli, Pseudomonas* species, and *Salmonella* species. Specific examples of infectious bacteria include but are not limited to: *Helicobacter pyloris, Borelia burgdorferi, Legionella pneumophilia, Mycobacteria* species (e.g., *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic species), *Streptococcus pneumoniae*, pathogenic *Campylobacter* species, *Enterococcus* species, *Haemophilus influenzae, Bacillus antracis, Corynebacterium diphtheriae, Erysipelothrix rhusiopathiae, Clostridium perfringers, Clostridium tetani, Enterobacter aerogenes, Klebsiella pneumoniae, Pasturella multocida, Bacteroides* species, *Fusobacterium nucleatum, Streptobacillus moniliformis, Treponema pallidium, Treponema pertenue, Leptospira* species, *Rickettsia* species, and *Actinomyces israelli*. Additional exemplary bacteria are *Mycoplasma*, e.g., *Mycoplasma pneumoniae, Chlamydophila*, e.g., *Chlamydophila pneumoniae, Bartonella* species, and *Tropheryma whippelii*.

Therapeutic Applications

Aspects of the invention include treating subjects infected with, and/or subjects at risk of developing, a microbial infection, particularly a drug-resistant microbial infection. A subject may be a vertebrate, a mammal, a bird, a reptile, a primate, or other vertebrate or multicellular organism. A subject may be a human. A subject may be a pet or a farm animal.

Accordingly, aspects of the invention include treating one or more conditions (e.g., diseases) or symptoms associated with a microbial infection. Microbial infections include but are not limited to wound infections, respiratory infections, systemic infections, skin infection, sexually transmitted diseases, gastrointestinal, urogenitary infections, pneumonia, tuberculosis, gonorrhea, syphilis, sepsis, meningitis, cholera, and diarrhea associated with a microbial infection.

The terms "treatment" and "treating" are intended to encompass also prophylaxis, therapy and cure. Accordingly, in one aspect, a treatment involves preventing or delaying or slowing the onset of a condition, disease, or disorder (e.g. the symptoms associated with the disease, condition, or disorder) associated with antibiotic resistant bacteria. In another aspect, a treatment involves treating (e.g. minimizing or reducing or slowing the development or reversing) an existing condition, disease, or disorder (e.g. the symptoms associated with the disease, condition, or disorder) associated with antibiotic resistant bacteria. In one embodiment, a treatment provides a cure for a condition, disease, or disorder.

Pharmaceutical Preparations

In another aspect, the present invention provides pharmaceutically acceptable compositions, which comprise a therapeutically effective amount of one or more of the compounds and/or compositions described herein, formulated together with one or more pharmaceutically acceptable carriers (additives) and/or diluents. As described in detail, the pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound and/or composition from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Examples of such formulations include, but are not limited to DMSO, 10 mM DMSO, 8% hydroxypropyl-beta-cyclodextrin in PBS, propylene glycol, etc.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

As set out herein, certain embodiments of the present compounds may contain a basic functional group, such as amino or alkylamino, and are, thus, capable of forming pharmaceutically-acceptable salts with pharmaceutically-acceptable acids. Certain embodiments may contain heavy metals that can form salts. The term "pharmaceutically-acceptable salts" in this respect refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19.)

Pharmaceutically acceptable salts of the subject compounds and/or compositions may include one or more conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants also can be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration, and other factors. The amount of active ingredient that can be combined with a carrier material to produce a single dosage form will generally be that amount of the compound and/or the composition which produces a therapeutic effect. Generally, this amount will range from about 1% to about 99% of active ingredient, preferably from about 5% to about 70%, most preferably from about 10% to about 30%.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound and/or a composition of the present invention. In certain embodiments, an aforementioned formulation renders orally bioavailable a compound and/or a composition of the present invention.

Methods of preparing these formulations or compositions may include the step of bringing into association a compound and/or a composition of the present invention with the carrier and, optionally, one or more accessory ingredients. In general, the formulations may be prepared by uniformly and intimately bringing into association a compound and/or a composition of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound and/or a composition of the present invention as an active ingredient. A pharmaceutical composition of the present invention also may be administered as a bolus, electuary or paste.

In solid dosage forms of the invention for oral administration (capsules, tablets, pills, dragees, powders, granules and the like), the active ingredient may be mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered a compound and/or a composition is moistened with an inert liquid diluent.

The tablets, and other solid dosage forms of pharmaceutical compositions of the present invention, such as dragees, capsules, pills and granules, optionally may be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter (and/or a filter that retains viruses and/or other microorganisms), or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of a compound and/or a composition of the invention may include pharmaceutically acceptable emulsions, microemulsions, solutions, suspensions, syrups and/or elixirs. In addition to the active ingredient, a liquid dosage form may contain one or more inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, oral compositions also can include one or more adjuvants such as wetting agents, emulsifying and suspending agents, sweetening, flavoring, coloring, perfuming and preservative agents.

Suspensions, in addition to the active compounds and/or a compositions, may contain one or more suspending agents as, for example, ethoxylated isostearyl alcohols, polyoxyethylene sorbitol and sorbitan esters, microcrystalline cellulose, aluminum metahydroxide, bentonite, agar-agar and/or tragacanth, and/or mixtures thereof.

Formulations of pharmaceutical compositions of the invention for rectal or vaginal administration may be presented as a suppository, which may be prepared by mixing one or more compounds and/or a compositions of the invention with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound and/or composition.

Formulations of the present invention that are suitable for vaginal administration also include pessaries, tampons, creams, gels, pastes, foams or spray formulations containing such carriers as are known in the art to be appropriate.

Dosage forms for the topical or transdermal administration of a compound and/or a composition of this invention may include powders, sprays, ointments, pastes, creams, lotions, gels, solutions, patches and inhalants. The active compounds and/or a compositions may be mixed under sterile conditions with a pharmaceutically-acceptable carrier, and with any preservatives, buffers, or propellants which may be required.

The ointments, pastes, creams and gels may contain, in addition to active compounds and/or compositions of this invention, excipients, such as animal and vegetable fats, oils, waxes, paraffins, starch, tragacanth, cellulose derivatives, polyethylene glycols, silicones, bentonites, silicic acid, talc and/or zinc oxide, or mixtures thereof.

Powders and sprays can contain, in addition to a compound and/or a composition of this invention, excipients such as lactose, talc, silicic acid, aluminum hydroxide, calcium silicates and/or polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound and/or a composition of the present invention to the body. Such patches can be made by dissolving or dispersing the compound and/or the composition in the proper medium. Absorption enhancers can also be used to increase the flux of the compound and/or the composition across the skin. Either providing a rate controlling membrane or dispersing the compound and/or the composition in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration may comprise one or more compounds and/or compositions of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and/or by the use of surfactants.

These compositions may also contain adjuvants such as preservatives, wetting agents, emulsifying agents and/or dispersing agents. Prevention of the action of microorganisms upon the subject compounds and/or compositions may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and/or gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms may be made by forming microencapsuled matrices of the subject compounds and/or compositions in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations also may be prepared by entrapping the drug in liposomes or microemulsions, which are compatible with body tissue.

In another aspect, the present invention relates to a method of treating a condition associated with antibiotic resistant bacteria. In particular, the invention provides methods for treating a condition associated with antibiotic resistant bacteria in a subject, comprising the step of administering to said subject a therapeutically effective amount of a pharmaceutical composition of the present invention. In certain embodiments, the condition associated with antibiotic resistant bacteria is a respiratory infection, pneumonia, anthrax, typhus, spotted fever, Q fever, plague, tularemia, or Lyme disease. In certain embodiments, the subject is a mammal, such as primate, canine or feline subject. In other embodiments, the subject is a human subject.

The phrase "therapeutically-effective amount" as used herein means that amount of a compound and/or a composition, material, or composition comprising a pharmaceutical composition of the present invention which is effective for producing some desired therapeutic effect in at least a subpopulation of cells in an animal at a reasonable benefit/risk ratio applicable to any medical treatment. A therapeutically effective amount is an amount sufficient to inhibit bacterial survival in at least a subset of cells that were exposed to antibiotic resistant bacteria. Accordingly, a therapeutically effective amount prevents or minimizes disease progression associated with antibiotic resistant bacteria. Disease progression can be monitored relative to an expected disease progression that is based on population studies, controlled observations in individuals, or a combination of both.

In certain embodiments, a pharmaceutical composition of the invention is administered orally. In other embodiments, a pharmaceutical composition of the invention is administered intravenously. Alternative routes of administration may be but are not limited to sublingual, intramuscular, and/or transdermal administrations.

When the pharmaceutical compositions of the present invention are administered to humans and animals, they can be given per se or as a pharmaceutical composition containing, for example, 0.1% to 99.5% (more preferably, 0.5% to 90%) of active ingredient in combination with a pharmaceutically acceptable carrier. Compounds and/or compositions of the invention may be of substantial purity, e.g. substantially free of reaction side-products, for example 0.1% to 99.5% pure, and more preferably, 0.5% to 90% pure.

Pharmaceutical compositions of the present invention may be given orally, parenterally, topically, or rectally. They are of course given in forms suitable for each administration route. For example, they may be administered in tablets or capsule form, by injection, inhalation, eye lotion, ointment, suppository, etc. (e.g. administration by injection, infusion or inhalation; topical by lotion or ointment; and rectal by suppositories.) In certain embodiments, oral administrations may be preferred.

The phrases "parenteral administration" and "administered parenterally" as used herein mean modes of administration other than enteral and topical administration, usually by injection, and may include, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal and/or intrasternal injection and/or infusion.

The phrases "systemic administration," "administered systemically," "peripheral administration" and "administered peripherally" as used herein mean the administration of a compound and/or a composition, drug or other material other than directly into the central nervous system, such that it enters the patient's system and, thus, is subject to metabolism and other like processes, for example, subcutaneous administration.

Pharmaceutical compositions may be administered to humans and other animals for therapy by any suitable route of administration, including orally, nasally, as by, for example, a spray, rectally, intravaginally, parenterally, intracisternally and topically, as by powders, ointments or drops, including buccally and/or sublingually.

Regardless of the route of administration selected, pharmaceutical compositions of the present invention, which may be used in a suitable hydrated form, may be formulated into pharmaceutically-acceptable dosage forms by conventional methods known to those of skill in the art.

Actual dosage levels of the active ingredients in pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular pharmaceutical compositions of the present invention employed, or the ester, salt or amide thereof, the route of administration, the time of administration, the rate of excretion or metabolism of the particular pharmaceutical compositions being employed, the duration of the treatment, other drugs, compounds and/or compositions and/or materials used in combination with the particular pharmaceutical compositions employed, the age, sex, weight, condition, general health and prior medical history of the patient being treated, and like factors well known in the medical arts. A daily, weekly, or monthly dosage (or other time interval) can be used.

A physician or veterinarian having ordinary skill in the art can readily determine and prescribe an effective amount of a pharmaceutical composition of the invention. For example, the physician or veterinarian could start doses of the compounds and/or compositions of the invention employed in the pharmaceutical composition at levels lower than that required to achieve the desired therapeutic effect and then gradually increase the dosage until the desired effect is achieved.

In general, a suitable daily dose of a pharmaceutical composition of the invention will be that amount of the pharmaceutical composition that is the lowest dose effective to produce a therapeutic effect. Such an effective dose will generally depend upon the factors described above. Generally doses of compounds and/or compositions of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight. It should be appreciated that the amount of toxic compound may be different from the amount of antimicrobial agent. Accordingly, both may be used at doses described herein.

If desired, the effective daily dose of the pharmaceutical compositions may be administered as two, three, four, five, six or more sub-doses administered separately at appropriate intervals throughout the day, optionally, in unit dosage forms.

In another aspect, the present invention provides pharmaceutically acceptable compositions which comprise a therapeutically-effective amount of one or more of the subject compounds and/or compositions, as described above, formulated together with one or more pharmaceutically acceptable carriers (additives) and/or diluents. As described in detail below, pharmaceutical compositions of the present invention may be specially formulated for administration in solid or liquid form, including those adapted for the following: oral administration, for example, drenches (aqueous or non-aqueous solutions or suspensions), tablets, boluses, powders, granules, pastes for application to the tongue; parenteral administration, for example, by subcutaneous, intramuscular or intravenous injection as, for example, a sterile solution or suspension; topical application, for example, as a cream, ointment or spray applied to the skin, lungs, or oral cavity; or intravaginally or intrarectally, for example, as a pessary, cream or foam; sublingually; ocularly; transdermally; nasally; pulmonary or to other mucosal surfaces.

Pharmaceutical compositions according to the invention may be formulated for administration in any convenient way for use in human or veterinary medicine, by analogy with other pharmaceuticals.

Kits

The invention also provides kits including one or more pharmaceutical compositions of the invention. A kit can also include one or more additional agents or compounds and/or compositions described herein. The different components of the kit can be provided in different containers. The kit can be compartmentalized to receive the containers in close confinement. The kit can also contain instructions for using the pharmaceutical compositions according to the invention.

As used herein, a kit such as a compartmentalized kit includes any kit in which compounds and/or compositions or agents are contained in separate containers. Illustrative examples of such containers include, but are not limited to, small glass containers, plastic containers or strips of plastic or paper. Particularly preferred types of containers allow the skilled worker to efficiently transfer reagents from one compartment to another compartment such that the samples and reagents are not cross-contaminated and the agents or solutions of each container can be added in a quantitative fashion from one compartment to another. Such containers include, but are not limited to, a container that will accept a compound or combination of compounds and/or other agents of the invention. One or more compounds or agents can be provided as a powder (e.g. a lyophilized powder) or precipitate. Such a compound and/or a composition can be resuspended prior to administration in a solution that may be provided as part of the kit or separately available. A kit can contain compounds and/or compositions or agents in other forms such as liquids, gels, solids, as described herein. Different compounds and/or a compositions and/or agents may be provided in different forms in a single kit.

This invention is not limited in its application to the details of construction and the arrangement of components set forth in the description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference. In case of conflict, the present description, including any definitions herein, will control.

EXAMPLES

The following examples illustrate certain aspects of the invention and are not limiting. In the examples, different strains of tetracycline-resistant *E. coli* were sensitized to a toxic compound using tetracycline, regardless of whether the tetracycline-resistance gene was carried on the bacterial chromosome or on an autonomous plasmid. In certain experiments, the order of treatment was important, and cells exposed first to cisplatin and then to tetracycline were less sensitized. In certain experiments, other antibiotics (ampicillin, kanamycin, and chloramphenicol) were tested with respective antibiotic-resistant bacteria and did not produce the same degree of sensitization to cisplatin. Therefore, in one embodiment, sensitization to cisplatin may involve an unexpected synergistic relationship among cisplatin, tetracycline and the tetracycline resistance gene.

Example 1

Tetracycline Resistance Determinant of Transposon Tn10 Confers High Sensitivity to Cisplatin in E. coli Materials and Methods
Bacterial Strains and Reagents The genotypes of the E. coli K-12 strains used for this work are listed in Table 1. Strain GM4292 was constructed by mating exponentially growing XL1-Blue (Stratagene) with MG1655 (both at $1\text{-}2 \times 10^8$/ml at a 1:1 ratio) for 60 min and plating dilutions of the mixture on MacConkey agar-tetracycline plates. A red tetracycline-resistant, nalidixic acid-sensitive colony was selected, purified and designated GM4292. Strain GM4293 was constructed by introducing F'42 (F'lac$^+$) from AB 1874 into KM81 by conjugation as described above and selecting for Lac$^+$ Str$^R$ colonies. A purified Lac$^+$ Str$^R$ recombinant overnight culture was diluted and plated on MacConkey agar-kanamycin and following incubation overnight at 37° C., white colonies were selected. White colonies can arise either by gene conversion, where the lac$^+$ allele on the F'42 plasmid is converted to lacZ::Kan, or by loss of the F'lac$^+$. The white colonies were tested for their ability to transfer kanamycin-resistance at high frequency to MG1655, indicating retention of the F' plasmid. One of these MG1655 recipients was designated GM4293.

Strains carrying the pBR322 plasmid were created using a standard transformation by electroporation protocol. Briefly, cells were grown to mid-log phase, spun down, and washed 3 times in ice-cold sterile water. Cells were then resuspended in the final volume of 100 μl of ice-cold sterile water, and 10 μg pBR322 (New England BioLabs) was added. The BTX electroporation system, ElectroCell Manipulator 600, was used to deliver the pulse. After the pulse, cells were immediately resuspended in 1 ml of LB broth. Appropriate dilutions of cells were prepared in M9 minimal salts, plated on LB-ampicillin plates, and allowed to form colonies overnight.

MacConkey agar and LB broth were purchased from Difco. LB broth contained 10 g tryptone, 5 g yeast extract, and 10 g NaCl per 1 L. All antibiotics and cisplatin (cis-diammine-dichloro-platinum(II), or CDDP) were purchased from Sigma-Aldrich. Antibiotics were used at the following final concentrations: 15 μg/ml tetracycline (Tc), 100 μg/ml ampicillin, 50 μg/ml kanamycin, 100 μg/ml streptomycin, 30 μg/ml nalidixic acid and 20 μg/ml chloramphenicol. Cisplatin solutions were prepared by dissolution in phosphate buffered saline (PBS) at 37° C. for one hour with rotation, filtering the solution through a 0.2 μm Acrodisc filter, and determining the concentration by UV absorbance at $A_{301}$ using a Beckmann DU-65 spectrophotometer. Appropriate doses of cisplatin were then prepared by dilution in PBS.

TABLE 1

The genotypes of the E. coli strains.

| Strain | Genotype |
| --- | --- |
| AB1157 | thr-1 araC14 leuB6(Am) Δ(gpt-proA)62 lacY1 tsx-33 supE44(AS) galK2(Oc) hisG4(Oc) rfbD1 mgl-51 rpoS396(Am) rpsL31(Str$^R$) kdgK51 xylA5 mtl-1 argE3(Oc) thi-1 |
| GM4799 | As AB1157 but mutS458::mTn10Kan |
| GM7698 | As AB1157 but ΔmutS465::Tet |
| GM7330 | Δ(lacY-lacZ)286 (φ80dIIΔ lacZ9) ara thi |

TABLE 1-continued

The genotypes of the E. coli strains.

| Strain | Genotype |
| --- | --- |
| GM7619 | As GM7330 but fpg::Tn10 |
| GM8085 | As GM7330 but Δfpg::Amp |
| CC104 | F'lacI$^q$ lacZ$^-$ proAB$^+$lara thi Δ(gpt-lac)5 |
| CC104mutY | As CC104 but mutY::mTn10 |
| MV4706 | As CC104 but ΔmutY::Cam |
| MG1655 | rph-1 |
| XL1-Blue | recA1 endA1 gyrA96 (Nal$^R$) thi-1 hsdR17 supE44 relA1 lac [F' proAB lacI$^q$Z ΔM15 Tn10 (Tet$^R$)] |
| GM4292 | As MG1655 but F'::Tn10 lacI$^q$ lacZΔM15 proAB$^+$ |
| GM4293 | As MG1655 but F'42 lacZ::Kan |
| AB1874 | F'42 (F'lac$^+$)/lac-19 |
| KM81 | As AB1157 but lacZ::Kan |

Survival Curves

Cells were grown overnight from single colonies in LB broth. The next morning, saturated overnight cultures were diluted 1:100 and grown for two hours to mid-log phase (cell density approximately $3 \times 10^8$ cells/ml). At this time, the cells were spun down, resuspended in M9 minimal salts, and treated with various concentrations of cisplatin at 37° C. for 1 hour. Exposure to cisplatin was stopped by dilution of the cells 1:100 in M9 salts. Appropriate serial dilutions were prepared for each dose and plated on LB plates or LB/Tet plates. Colonies were counted the next day after incubation at 37° C. Survival was calculated as a percentage of cells forming colonies in treated populations relative to untreated.

Atomic Absorption Spectrometry

For atomic absorption experiments, cells were grown and treated according to the procedure outlined above. Appropriate serial dilutions were prepared and the cells plated on LB plates to determine cell counts. After cisplatin treatment, the cells were washed in M9 minimal salts and then lysed using Bio-Rad cell lysis solution. The platinum content was determined by atomic absorption spectrometry using a Perkin Elmer AAnalyst-300 spectrometer equipped with a HGA-800 graphite furnace system and AS-72 autosampler.

For assessment of DNA platinum adduct levels, DNA isolation was carried out according to manufacturer's instructions using Bio-Rad AquaPure Genomic DNA Isolation Kit, and the DNA concentration was determined by UV absorbance at $A_{260}$ using a Beckmann DU-65 spectrophotometer. Platinum content was measured by atomic absorption spectrometry as specified above.

Results

It was observed that the presence of tetracycline in the growth medium of the MG1655 carrying an F'Tn10 plasmid affected strain survival upon subsequent treatment with cisplatin (FIG. 2a). When MG1655/F'Tn10 cells were grown without tetracycline, their survival upon exposure to cisplatin was not different from that of MG1655 wild-type cells not carrying the plasmid. However, when tetracycline was present in the growth medium of overnight and log phase cultures of the MG1655/F'Tn10, subsequent treatment with cisplatin caused a dramatic decrease in survival of these tetracycline-resistant bacteria. In similar experiments with MG1655/F'Tn10::kan, the presence of kanamycin in the growth medium of overnight and log phase cultures did not affect the survival upon treatment with cisplatin, as compared to MG1655 (FIG. 2b). These results indicated that sensitization of bacteria to cisplatin was caused by the presence of tetracycline in the growth medium, while neither the F' plasmid itself, nor the presence of kanamycin in the growth medium had affected the sensitivity of E. coli to cisplatin.

Sensitization of bacteria to cisplatin by tetracycline was also observed when the Tn10 tet genes were present in the bacterial chromosome rather than on the F' plasmid (FIG. 3). We tested three pairs of DNA repair mutants in three different genetic backgrounds, and in each case we observed that the presence of tetracycline, but not other antibiotics, in the growth medium sensitized them to subsequent cisplatin treatment. Survival of CC104 mutY::cam, GM7330 fpg::amp and AB1157 mutS::kan mutants was not affected by the presence or absence of chloramphenicol, ampicillin, and kanamycin, respectively, in the growth medium. However, survival of tetracycline-resistant CC104 mutY::tet, GM7330 fpg::tet and AB1157 mutS::tet mutants upon treatment with cisplatin dramatically decreased when these mutants were grown with tetracycline, while their survival was not different from respective wild-types when tetracycline was absent from the growth medium.

The sensitization of tetracycline-resistant bacteria to cisplatin by tetracycline pre-treatment, however, appeared to be dependent on the type of tet gene. The pBR322 tet gene did not produce similar sensitization to cisplatin in AB1157, CC104 or MG1655-cells carrying pBR322 when they were grown with tetracycline prior to cisplatin treatment (FIG. 4).

Treatment with tetracycline did not appear to have any effect on survival of tetracycline-resistant cells when it was applied after cisplatin exposure (FIG. 5). In these experiments, tetracycline-resistant cells were grown either with or without tetracycline, treated with cisplatin, and then plated on either LB or LB/Tet plates. Survival of Tn10 tet gene-carrying cells was not different from the wild-type when they were grown without tetracycline, and decreased when they were grown with tetracycline. However, in each instance survival rates were not affected by post-treatment with tetracycline, i.e., survival was identical on LB and on LB/Tet plates.

Figure 6:
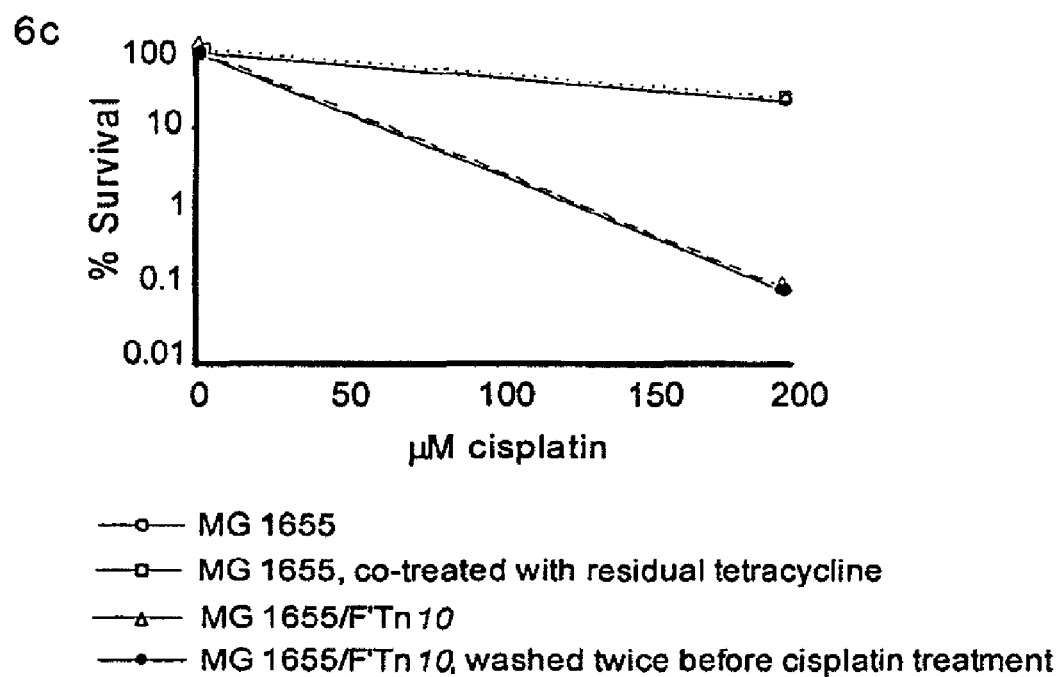
FIG. 6 is (a,b) a schematic depicting possible mechanisms of cisplatin toxicity in tetracycline resistant bacteria, and (c) a graph that shows the residual quantities of tetracycline present at the time of cisplatin treatment do not affect survival of MG1655 and MG1655/F'Tn10 carrying cells.

Residual quantities of tetracycline present at the time of cisplatin treatment had no effect on survival, as demonstrated by experiments where tetracycline was either added to wild-type cells, or washed out of tetracycline-resistant cells grown in tetracycline, at the time of cisplatin treatment (FIG. 6c). Addition of tetracycline to wild-type cells during cisplatin treatment did not affect their survival, and washing the residual tetracycline out of tetracycline-resistant cells before cisplatin treatment did not improve their survival. These observations suggest that residual tetracycline present at the time of cisplatin treatment could not have been responsible for the increased toxicity in tetracycline-resistant cells grown with tetracycline prior to cisplatin treatment.

Additional sensitization to cisplatin by tetracycline was observed in experiments where tetracycline-resistant bacteria were grown with tetracycline and then co-treated with cisplatin in the presence of tetracycline. We observed an additional 100-fold decrease in survival in tetracycline-resistant cells that were not only pre-treated, but also co-treated with tetracycline (FIG. 7). Interestingly, this effect was observed in MG1655 cells carrying either F'Tn10 or pBR322, unlike the pre-treatment sensitization, which was observed only with the Tn10 tet gene, but not the pBR322 tet gene.

Sensitization to cisplatin by co-treatment was not dependent on the presence of tetracycline in the growth medium, and was also observed with both Tn10 and pBR322 tet genes (FIG. 8). In these experiments, tetracycline-resistant cells were grown without tetracycline, and then treated either with cisplatin alone, or with cisplatin in the presence of tetracycline. We observed that when treated with cisplatin alone, MG1655 cells carrying either F'Tn10 or pBR322 tet genes were equally sensitive to cisplatin as MG1655 cells not carrying any tet genes. However, when cells carrying either plasmid were treated with cisplatin in the presence of tetracycline, their survival decreased.

One possible explanation of our results could be that the role of the tet gene-encoded antiporter in observed toxicity was to increase the cellular concentration of cisplatin. To test this possibility, we determined the amount of cisplatin in MG1655 and tetracycline-induced MG1655/F'Tn10 cells, at the highest cisplatin dose used in our experiments (FIG. 9). We found that platinum levels were the same in MG1655 and in MG1665/F'Tn10 cells that were grown in tetracycline prior to cisplatin treatment (FIG. 9d). Co-treatment with tetracycline, however, was accompanied by a small increase in total cellular levels of cisplatin in MG1655/F'Tn10, but not in MG1655 cells.

Next the levels of cisplatin DNA damage were determined by assessing the platinum content in DNA isolated from MG1655 and MG1655/F'Tn10 cells induced with tetracycline (FIG. 9e). It was found that at the highest dose used in this experiment, MG1655/F'Tn10 cells grown with tetracycline accumulated more DNA damage than MG1655 cells, and that co-treatment with tetracycline was associated with a small further increase in levels of DNA damage in MG1655/F'Tn10 cells, but not in MG1655 cells.

Figure 10:
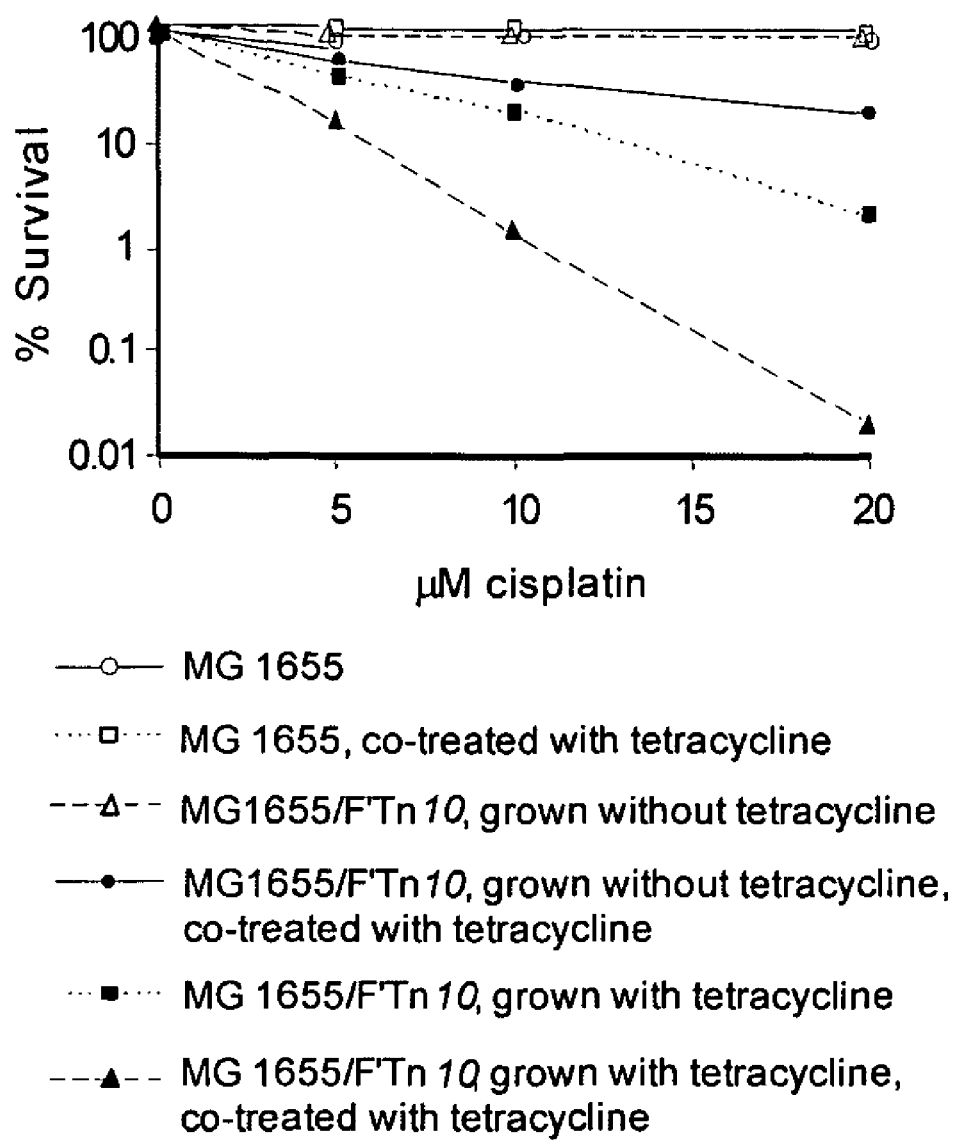
FIG. 10 is a graph that shows the survival of MG1655 and MG1655/F'Tn10 upon prolonged (4 hours) exposure to 10-fold lower doses of cisplatin.

Prolonged (4 hours) treatment with 10-fold lower doses of cisplatin produced results that paralleled those obtained by 1 hour treatment with higher doses (FIG. 10). Tetracycline-resistant cells that were grown (pre-treated) with tetracycline and then co-treated with cisplatin and tetracycline were the most sensitive to cisplatin treatment. Tetracycline-resistant cells that were either pre-treated or co-treated with tetracycline were also more sensitive to cisplatin than wild-type, with pre-treatment having a more pronounced effect of sensitization than co-treatment. Finally, cisplatin treatment of tetracycline-resistant cells that were neither pre-treated nor co-treated with tetracycline resulted in survival that was not different from survival of wild-type cells.

Example 2

Treatment of Patients Infected with Tetracycline Resistant Microorganisms

Patients infected with tetracycline resistant microorganisms maybe treated with a pharmaceutical composition of 10-1000 mg/day, or about 100 mg/day of tetracycline and 1-100 mg/day or about 10 mg/day of cisplatin for at least seven, ten or fourteen days. Following the treatment the patients are cured of the infection with the tetracycline resistant microorganisms.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims.

What is claimed is:

1. A method of treating an antibiotic-resistant bacterial infection in a subject, the method comprising administering to a subject suspected of having an antibiotic-resistant bacterial infection a therapeutically effective combination of tetracycline and cisplatin.

2. The method of claim 1, wherein the antibiotic-resistant bacterial infection is a tetracycline-resistant bacterial infection.

3. The method of claim 1, wherein the antibiotic-resistant bacterial infection is a multi-drug-resistant bacterial infection.

4. The method of claim 3, wherein the multi-drug resistance includes tetracycline resistance.

5. The method of claim 1, wherein the subject is a human.

6. The method of claim 1, wherein the subject has a condition associated with a bacterial infection selected from the group consisting of a gastrointestinal infection, urogenitary infection, respiratory infection, a skin infection, a systemic infection, a wound infection and a sexually transmitted disease.

7. The method of claim 1, wherein a pharmaceutical composition comprising tetracycline and cisplatin is administered to the subject.

8. The method of claim 7, wherein the pharmaceutical composition is administered via a route chosen from oral, parenteral, topical, ocular, transdermal, and nasal routes.

9. The method of claim 7, wherein the pharmaceutical composition is administered by subcutaneous, intramuscular, intravenous, or epidural injection.

10. A method of killing or inhibiting the growth of antibiotic-resistant bacteria, the method comprising contacting the bacteria with a combination of tetracycline and cisplatin, wherein the combination kills or inhibits growth of the bacteria.

11. The method of claim 10, wherein the bacteria are is contacted with tetracycline before being contacted with cipl-atin.

* * * * *

UNITED STATES PATENT AND TRADEMARK OFFICE
CERTIFICATE OF CORRECTION

PATENT NO. : 7,943,600 B2  
APPLICATION NO. : 11/314186  
DATED : May 17, 2011  
INVENTOR(S) : Doriana Froim et al.

Page 1 of 1

It is certified that error appears in the above-identified patent and that said Letters Patent is hereby corrected as shown below:

Column 28, claim 11, line 12, delete "is";

Column 28, claim 11, lines 13-14, replace "ciplatin" with "cisplatin".

Signed and Sealed this
Second Day of August, 2011

David J. Kappos
*Director of the United States Patent and Trademark Office*